(12) United States Patent
Nakano et al.

(10) Patent No.: US 10,928,385 B2
(45) Date of Patent: Feb. 23, 2021

(54) INTERACTION ENERGY CALCULATION SYSTEM, METHOD, AND PROGRAM

(75) Inventors: Tatsuya Nakano, Tokyo (JP); Yuji Mochizuki, Tokyo (JP); Kaori Fukuzawa, Tokyo (JP)

(73) Assignees: JAPAN AS REPRESENTED BY DIRECTOR GENERAL OF NATIONAL INSTITUTE OF HEALTH SCIENCES; RIKKYO GAKUIN; MIZUHO INFORMATION & RESEARCH INSTITUTE, INC.

( * ) Notice: Subject to any disclaimer, the term of this patent is extended or adjusted under 35 U.S.C. 154(b) by 1054 days.

(21) Appl. No.: 14/356,744

(22) PCT Filed: Aug. 6, 2012

(86) PCT No.: PCT/JP2012/069943
§ 371 (c)(1),
(2), (4) Date: Aug. 26, 2014

(87) PCT Pub. No.: WO2013/069348
PCT Pub. Date: May 16, 2013

(65) Prior Publication Data
US 2014/0372047 A1 Dec. 18, 2014

(30) Foreign Application Priority Data
Nov. 9, 2011 (JP) .............................. JP2011-245411

(51) Int. Cl.
*G01N 33/53* (2006.01)
*G16C 10/00* (2019.01)

(52) U.S. Cl.
CPC ............. *G01N 33/53* (2013.01); *G16C 10/00* (2019.02); *G01N 2500/20* (2013.01)

(58) Field of Classification Search
None
See application file for complete search history.

(56) References Cited

PUBLICATIONS

International Search Report for corresponding PCT/JP2012/069943, dated Sep. 11, 2012 from the JPO.
Fujita, et al.: "*Accuracy of Fragmentation in AB Initio Calculations of Hydrated Sodium Cation*", Chemical Physics Letters, Aug. 27, 2009, vol. 478, No. 4-6, p. 295-300.
Hitaoka, et al.: "*Correlation Analyses on Binding Affinity of Sialic Acid Analogues with Influenza Virus Neuraminidase*", Journal of Chemical Information Modeling, 2010, vol. 50, No. 10, p. 1796-1805.
Watanabe, et al.: "*New Fragmentation of Fragment Molecular Orbital Method Applicable to Fragment Based Drug Design*", Nov. 8, 2011, ROMBUNNO.CBI-P1-14.

Yoshioka, et al.: "*Prediction of Probable Mutations of Influenza Virus Hemagglutinin Protein Based on Large-Scale AB Initio Fragment Molecular Orbital Calculations*", Journal of Molecular Graphics and Modelling, Sep. 2011, vol. 30, p. 110-119.
IPRP from corresponding PCT/JP2012/069943, dated May 13, 2014, by Yukari Nakamura of the International Bureau of WIPO.
S. Anzaki, C. Watanabe, K. Fukuzawa, Y. Mochizuki, S. Tanaka (2014). "Interaction Energy Analysis on Specific Binding of Influenza Virus Hemagglutinin to Avian and Human Sialosaccharide Receptors: Importance of Mutation-Induced Structural Change," J. Mol. Graph. Model. 53 48-58 Jul. 2014.
C. Watanabe, K. Fukuzawa, S. Tanaka, and S. Aida-Hyugaji (2014). "Charge Clamps of Lysines and Hydrogen Bonds Play Key Roles in the Mechanism to Fix Helix 12 in the Agonist and Antagonist Positions of Estrogen Receptor a: Intramolecular Interactions Studied by the Ab Initio Fragment Molecular Orbital Method," J. Phys. Chem. B 118(19) 4993-5008 Apr. 2014.
Pruitt, S. et al. (2016). "Importance of Three-Body Interactions in Molecular Dynamics Simulations of Water Demonstrated with the Fragment Molecular Orbital Method," J. Chem. Theory and Comp. 2016, 12, 1423-1435.
K. Fukuzawa, C. Watanabe, I. Kurisaki, N. Taguchi, Y. Mochizuki, T. Nakano, S. Tanaka and Y. Komeiji (2014). "Accuracy of the Fragment Molecular Orbital (FMO) Calculations for DNA: Total Energy, Molecular Orbital, and Inter-Fragment Interaction Energy," Comp. Theor. Chem. 1034 7-16 Feb. 2014.
Y. Okiyama, T. Tsukamoto, C. Watanabe, K. Fukuzawa, S. Tanaka, Y. Mochizuki (2013). "Modeling of Silica-Peptide Interaction based on Four-Body Corrected Fragment Molecular Orbital (FMO4) Calculations," Chem. Phys. Lett. 566 25-31 2013.
K. Fukuzawa, I. Kurisaki, C. Watanabe, Y. Okiyama, Y. Mochizuki, S. Tanaka, Y. Komeiji (2014). "Explicit Solvation Modulates Intra- and Inter-Molecular Interactions within DNA: Electronic Aspects Revealed by the ab initio Fragment Molecular Orbital (FMO) method," Comp. Theor. Chem 1054 29-37 Dec. 2014.
C. Watanabe, K Fukuzawa, Y. Okiyama, T. Tsukamoto, A. Kato, S. Tanaka, Y. Mochizuki, and T. Nakano (2013). "Three- and Four-body Corrected Fragment Molecular Orbital Method with New Subdividing Fragmentation Applicable to Fragment-Based Drug Design," J. Mol. Graph. Model. 41 31-42 2013.
Takatoshi Fujita, Kaori Fukuzawa, Yuji Mochizuki, Tatsuya Nakano, Shigenori Tanaka (2009). "Accuracy of Fragmentation in ab initio Calculations of Hydrated Sodium Cation," Chemical Physics Letters 478 295-300 Jul. 2009.

(Continued)

*Primary Examiner* — Pablo S Whaley
(74) *Attorney, Agent, or Firm* — Tarolli, Sundheim, Covell & Tummino LLP

(57) ABSTRACT

A system computes the interaction energy between a plurality of fragments in a calculation object substance according to the fragment molecular orbital method. The energy of each fragment, the two-body interaction energy of each dimer including two fragments, and the three-body interaction energy of each trimer including three fragments are calculated. The two-body interaction energy of each dimer is corrected by adding, to the two-body interaction energy of the dimer, the contribution of the dimer in the three-body interaction energy of the trimer that includes the dimer.

9 Claims, 7 Drawing Sheets

(56) References Cited

PUBLICATIONS

S. Tanaka, Y. Mochizuki, Y. Komeiji, Y. Okiyama and K. FukuzawaS. Tanaka, Y. Mochizuki, Y. Komeiji, Y. Okiyama and K. Fukuzawa (2014). "Electron-Correlated Fragment-Molecular-Orbital Calculations for Biomolecular and Nano Systems," Phys. Chem. Chem. Phys 16(22) 10310-10344 2014.

K. Tokuda, C. Watanabe, Y. Okiyama, Y. Mochizuki, K. Fukuzawa and Y. Komeiji (2016). "Hydration of Ligands of Influenza Virus Neuraminidase Studied by the Fragment Molecular Orbital Method," J. Mol. Graph. Model. 69 153 Aug. 2016.

Masataka Sakaguchi, Yuji Mochizuki, Chiduru Watanabe, Kaori Fukuzawa (2015). "Effects of Water Molecules and Configurations of Neighboring Amino Acid Residues Surrounding DsRed Chromophore on Its Excitation Energy," Journal of Computer Chemistry, Japan 14(5) 155-163 Dec. 2015.

Koichiro Kato, Kaori Fukuzawa, Yuji Mochizuki (2015). "Modeling of Hydroxyapatite—Peptide Interaction based on Fragment molecular Orbital Method", Chemical Physics Letters 629 58-64 Apr. 2015.

R. Kurauchi, C. Watanabe, K. Fukuzawa and S. Tanaka. (2015). "Novel type of Virtual Ligand Screening on the basis of Quantum-Chemical Calculations for Protein Ligand Complexes and Extended Clustering Techniques," Comp. Theor. Chem 1061 12-22 Mar. 2015.

T. Tsukamoto, K. Kato, A. Kato, T. Nakano, Y. Mochizuki, K. Fukuzawa (2015). "Implementation of Pair Interaction Energy Decomposition Analysis and its Applications to Protein-Ligand Systems," Journal of Computer Chemistry, Japan 14(1) Jan. 9, 2015.

INTERACTION ENERGY CALCULATION SYSTEM, METHOD, AND PROGRAM

RELATED APPLICATION

This application claims priority from International Patent Application Serial No. PCT/JP2012/069943, filed 6 Aug. 2012; which claims priority from Japanese Serial No. 2011-245411, filed 9 Nov. 2011, both of which are incorporated herein in their entirety.

FIELD OF THE INVENTION

The present invention relates to a system, a method and a program for calculating inter-fragment interaction energy by using the fragment molecular orbital method.

BACKGROUND OF THE INVENTION

As a method for calculating the electronic state of a macromolecule such as a polymer, a fragment molecular orbital method (FMO method) has hitherto been widely used. For example, in the FMO methods described in Non-Patent Document 1 and Non-Patent Document 2, first, a polymer structure is divided into a plurality of fragments. Next, the electronic states in the monomers of the fragments and the electronic states in the dimers of the fragments are calculated. Then the electronic state of the whole molecule is calculated on the basis of the electronic states of these monomers and dimers. According to such an FMO method, the calculation cost is drastically reduced as compared to a method for calculating the electronic state of a whole molecule from the structure of the whole molecule, such as ab initio molecular orbital methods. Moreover, according to the FMO method, the inter-fragment interaction energies (IFIE) can be calculated, and hence types and degrees of the inter-fragment interactions can also be analyzed on the basis of the IFIEs. The PIE (Pair Interaction Energy) used in the FMO method is synonymous with the foregoing IFIE.

Recently, the foregoing FMO method has also been applied to the analysis of the interaction between the receptor, which is a biopolymer associated with disease, and a candidate compound of a ligand binding to the receptor. In this case, first, the receptor structure is divided into fragments each composed of an amino acid residue unit, and then the IFIE between each of the fragments of the receptor structure and the ligand (or the candidate compound thereof) structure, which is another fragment. On the basis of a comparison between the IFIEs thus obtained, the binding mechanism between the receptor and the ligand can be inferred, and hence the analysis of the interaction on the basis of the IFIEs is highly useful in performing a molecular design of a candidate compound of a ligand as a new medicine.

PRIOR ART DOCUMENTS

Non-patent Documents

Non-Patent Document 1: Nakano et al., J. Comput. Chem. Jpn., Vol. 6, No. 3, pp. 173-184 (2007)
Non-Patent Document 2: Fukuzawa et al., J. Comput. Chem. Jpn., Vol. 6, No. 3, pp. 185-198 (2007)

SUMMARY OF THE INVENTION

Between a receptor and a ligand, a plurality of interactions is found to occur in not a few cases. In this connection, for the purpose of finding the contribution degree of each of the sites of the ligand to each of interactions, there has been investigated a calculation in which both of the receptor structure and the ligand structure are each divided into a plurality of fragments, and the interaction energies between the fragments of the ligand and the receptor are calculated. According to this calculation, the contribution in each of the fragments of the ligand can be analyzed, and hence it becomes easier to select the candidate compounds for a new medicine on the basis of the binding mechanism between the receptor and the ligand.

However, in the FMO method, in which a molecular complex is treated as an aggregate of dimers, when the quantity of fragments is increased as described above, it sometimes becomes difficult to ensure accuracy of the IFIEs as the influence of the inter-fragment interactions are expanded. Consequently, even when the IFIEs are calculated according to the mode of the division of the ligand structure into fragments, no sufficient reliability can be obtained for the results of the analysis of the interactions, and eventually, there occurs a problem that no sufficient reliability can be obtained with respect to the rightness of the selection of the candidate compound.

When the ligand structure is divided into fragments, but also even when the ligand structure is not divided into fragments, the accuracy of the IFIE calculation is required to be improved in the analysis of the details of the interactions to be performed as described above. The foregoing problem is not limited to the case where the interaction energy between a receptor and a ligand is calculated, but also generally involved in common in the cases where the inter-fragment interaction energies in the calculation object substance are calculated by the FMO method, such as the case where the interaction energy between a carbon crystal and a protein is calculated by the FMO method.

An object of the present invention is to provide a system, a method and a program for an interaction energy calculation that are capable of improving the accuracy of the calculation of the inter-fragment interaction energies calculated by using the FMO method.

In accordance with one aspect of the present invention, an interaction energy calculation system is provided that includes a control unit for calculating inter-fragment interaction energies between a plurality of fragments in a calculation object substance by a fragment molecular orbital method. The control unit includes a first calculation section, a second calculation section, third calculation section, and a correction section. The first calculation section calculates the energy of each of the fragments. The second calculation section calculates the two-body interaction energy of each of a plurality of dimers. Each of the dimers includes two of the fragments. The third calculation section calculates the three-body interaction energy of each of a plurality of trimers. Each of the trimers includes three of the fragments. The correction section corrects the two-body interaction energy. For each dimer, the correction section adds, to the two-body interaction energy of the dimer, contribution of the dimer in the three-body interaction energy of the trimer including the dimer, thereby correcting the two-body interaction energy of the dimer, and calculates the corrected two-body interaction energy as inter-fragment interaction energy in the dimer.

In accordance with another aspect of the present invention, a method for calculating inter-fragment interaction energies between a plurality of fragments in a calculation object substance by a fragment molecular orbital method is provided. The method includes: a first calculation stage for calculating the energy of each of the fragments, a second calculation stage for calculating the two-body interaction energy of each of a plurality of dimers, each of the dimers including two of the fragments, a third calculation stage for calculating the three-body interaction energy of each of a plurality of trimers, each of the trimers including three of the fragments, and a correction stage for correcting the two-body interaction energy, wherein, for each dimer, the correction stage adds, to the two-body interaction energy of the dimer, contribution of the dimer in the three-body interaction energy of the trimer including the dimer, thereby correcting the two-body interaction energy of the dimer, and calculates the corrected two-body interaction energy as inter-fragment interaction energy in the dimer.

In accordance with a further aspect of the present invention, a non-transitory computer-readable recording medium is provided that stores a program for calculating inter-fragment interaction energies between a plurality of fragments by using a calculating system that includes a control section for calculating inter-fragment interaction energies between a plurality of fragments in a calculation object substance by a fragment molecular orbital method. When the program is executed, the computer-readable recording medium causes the control section to function as: a first calculation section for calculating the energy of each of the fragments, a second calculation section for calculating the two-body interaction energy of each of a plurality of dimers, each of the dimers including two of the fragments, a third calculation section for calculating the three-body interaction energy of each of a plurality of trimers, each of the trimers including three of the fragments, and a correction section for correcting the two-body interaction energy, wherein, for each dimer, the correction section adds, to the two-body interaction energy of the dimer, contribution of the dimer in the three-body interaction energy of the trimer including the dimer, thereby correcting the two-body interaction energy of the dimer, and calculates the corrected two-body interaction energy as inter-fragment interaction energy in the dimer.

DETAILED DESCRIPTION OF THE PREFERRED EMBODIMENTS

First Embodiment

An interaction energy calculation system, method and program according to a first embodiment of the present invention will now be described with reference to FIGS. 1 to 4. In the present embodiment, the FMO method taking two-body terms into account is referred to as the FMO2 method and the FMO method taking two-body terms and three-body terms is referred to as the FMO3 method.

Hereinafter, a molecular complex composed of a receptor composed of proteins and a compound (candidate compound) to be a candidate of the ligand binding to the receptor is taken as a calculation object substance, and a case where the interaction energies between the fragments of the receptor structure and the fragments of the candidate compound structure are calculated will be described.

Figure 1:
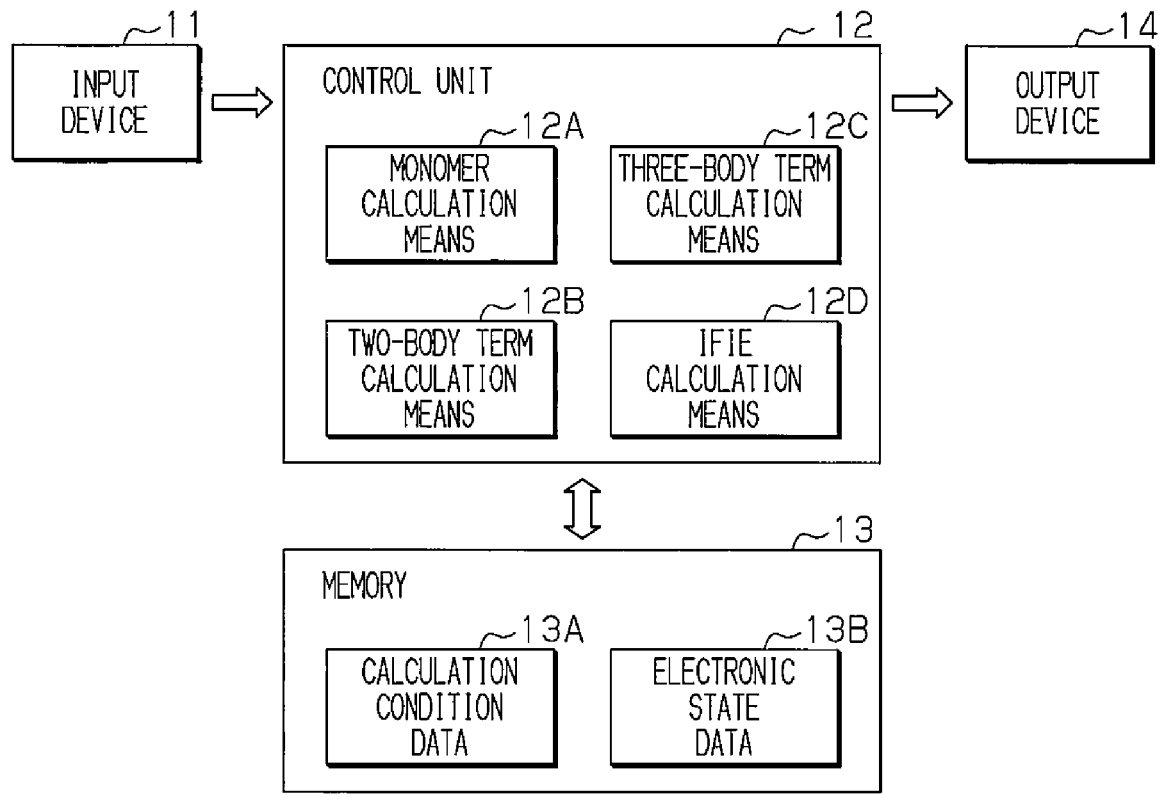
FIG. 1 is a functional block diagram illustrating an interaction energy calculation system according to a first embodiment of the present invention.

As shown in FIG. 1, the interaction energy calculation system of the present embodiment includes an input device 11, a control unit 12, a memory 13, and an output device 14.

The input device 11 includes, for example, a keyboard and a mouse, and inputs a set of calculation condition data indicating the calculation conditions of the interaction energy (energies) into the control unit 12. The control unit 12 causes the memory 13 to store the set of calculation condition data input into the control unit 12.

The control unit 12 includes a CPU, a RAM, and a ROM, and calculates, on the basis of the set of calculation condition data, the IFIEs, which are the interaction energies between the fragments of the receptor structure and the fragments of the candidate compound structure. In this case, the control unit 12 functions as a monomer calculation means 12A serving as a first calculation section, a two-body term calculation means 12B serving as a second calculation section, a three-body term calculation means 12C serving as a third calculation section, and an IFIE calculation means 12D serving as a correction section, by executing the interaction energy calculation program for calculating the IFIEs. The CPU of the control unit 12 may have a plurality of arithmetic cores, each of which executes the interaction energy calculation program, and thus may function as the monomer calculation means 12A, the two-body term calculation means 12B, the three-body term calculation means 12C, and the IFIE calculation means 12D. In this case, the calculations for a plurality of fragments are processed in parallel, and the time required for the calculation of the IFIEs is reduced.

Among these, the monomer calculation means 12A calculates, for the fragments of the receptor structure and the fragments of the candidate compound structure, the energy and the electron density of each of the monomers corresponding to these fragments (hereinafter, monomers). In this case, the monomer calculation means 12A calculates the environmental electrostatic potential of each of the monomers due to the other surrounding monomers, and further calculates the energy and the electron density of the monomer under the environmental electrostatic potential. The monomer calculation means 12A causes the memory 13 to store the calculated energies and electron densities of the monomers.

The two-body term calculation means 12B treats any two fragments as a dimer composed of the two fragments. Additionally, the two-body term calculation means 12B uses the calculation results of the monomer calculation means 12A, thus calculates the environmental electrostatic potential of each of the dimers due to the monomers surrounding the dimer, and further calculates the energy and the electron density of the dimer under the environmental electrostatic potential. The two-body term calculation means 12B causes the memory 13 to store the calculated energies and electron densities of the dimers.

The three-body term calculation means 12C treats any three fragments as a trimer composed of the three fragments. The three-body term calculation means 12C uses the calculation results of the monomer calculation means 12A, thus calculates the environmental electrostatic potential of each of the trimers due to the monomers surrounding the trimer, and further calculates the energy and the electron density of the trimer under the environmental electrostatic potential. The three-body term calculation means 12C causes the memory 13 to store the calculated energies and electron densities of the trimers.

In this case, the two-body term calculation means 12B calculates the energies and the electron densities of the dimers by using the FMO2 method. The three-body term calculation means 12C also calculates the energies and the electron densities of the trimers by using the FMO3 method. The calculation results of the two-body term calculation means 12B and the calculation results of the three-body term calculation means 12C are stored in the memory 13.

The IFIE calculation means 12D uses the energies of the dimers calculated by the two-body term calculation means 12B and the energies of the trimers calculated by the three-body term calculation means 12C, and thus calculates the IFIEs of a specific dimer. The IFIE calculation means 12D outputs the calculated IFIEs into the output device 14.

The memory 13 includes storages such as a RAM and a hard disk, and stores the set of calculation condition data 13A used for the calculation of the IFIEs, and the set of electronic state data 13B calculated by using the set of calculation condition data 13A.

The set of calculation condition data 13A includes the set of data related to the calculation method of the electronic state, the basis functions used for the calculation, the molecular structure of the complex including the receptor and the candidate compound, and the quantity of the fragments in the molecular complex. The set of calculation condition data 13A also includes the set of data related to the quantity of the atoms in each of the fragments, the quantity of the bonds between the fragments of each of a plurality of fragment pairs, the reference numbers of the atoms in each of the fragments, the reference number(s) of the atom(s) in each of the fragments, bonded to another fragment or other fragments, and the formal charge of each of the fragments. The set of calculation condition data 13A further includes the set of data indicating a specific dimer to be a calculation object of the interaction energy.

As the calculation methods of the electronic state, for example, the HF (Hartree-Fock) method, the MP2 (Moeller-Plesset second-order perturbation) method, and higher-order electron correlation methods are used. As the basis functions, for example, 6-31G and 6-31G* basis functions are used.

A set of molecular structure data includes the set of three-dimensional coordinate data representing the structure of the complex including the receptor and the candidate compound. Such a set of coordinate data is, for example, the set of data obtained by optimizing the set of coordinate data registered in the protein data base on the basis of the molecular mechanics calculation, the classical molecular dynamics calculation and the quantum chemical calculation.

The set of data of the quantity of the fragments includes the quantity of the fragments of the receptor structure and the quantity of the fragments of the candidate compound structure. For example, in the case where the receptor structure is divided into the amino acid residue units, the quantity of the fragments of the receptor structure is identical with the quantity of the amino acid residues in the receptor.

The set of data of the quantity of the atoms in the respective fragments includes the quantity of the atoms included in each of the fragments of the receptor structure, and the quantity of the atoms included in each of the fragments of the candidate compound structure.

The set of data of the quantity of the bonds between the fragments includes the quantity of the covalent bonds formed between each of the fragments and fragments other than the fragment, namely, the quantity of the covalent bonds broken when the receptor structure and the candidate compound structure are divided into fragments.

The set of data of the reference numbers of the atoms in the fragments is a set of reference numbers assigned to each of the fragments, and is a set of serial numbers associated with the respective atoms in each of fragments.

The set of data of the reference numbers of the atoms in each of the fragments bonded to other fragments is a set of reference numbers assigned to each of the fragments, and includes the reference numbers of the atoms that are bonded to the other fragments among the atoms in the fragment and the reference numbers of the atoms that are bonded to the fragment among the atoms in the other fragments.

The set of data related to the formal charges of the fragments means a set of data of the formal charges assigned to the respective fragments.

A set of fragment division information includes the quantity of the fragments, the quantity of the atoms in each of the fragments, the quantity of the inter-fragment bonds, the reference numbers of the atoms in each of the fragments, the reference number of the atoms in each of the fragments, bonded to other fragments and the formal charges in each of the fragments. The respective means constituting the control unit 12 refer to the set of fragment division information, and perform various calculations for each of the fragments specified on the basis of the set of fragment division information.

The set of electronic state data 13B includes the set of data related to the molecular orbitals of the fragments, the energies of the monomers, the electron densities of the monomers, the energies of the dimers, the electron densities of the dimers, the energies of the trimers and the electron densities of the trimers.

The set of data of the molecular orbitals, energies and electron densities of the monomers includes the energies and electron densities of the monomers calculated by the monomer calculation means 12A. The set of data of the energies and electron densities of the dimers includes the energies and electron densities of the dimers calculated by the two-body term calculation means 12B. The set of data of the energies and electron densities of the trimers includes the energies and electron densities of the trimers calculated by the three-body term calculation means 12C.

The output device 14 includes, for example, a display, and outputs the IFIE calculated by the IFIE calculation means 12D.

Next, the processing procedure in the calculation of the inter-fragment interaction energy by the foregoing interaction energy calculation system will be described with reference to FIGS. 2 to 4.

Figure 2:
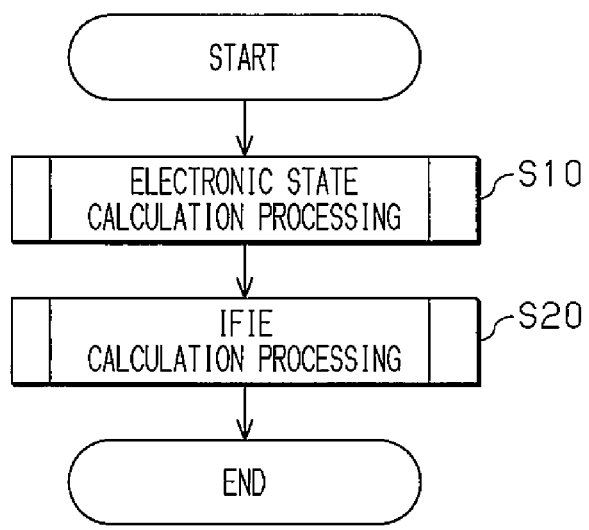
FIG. 2 is a flowchart illustrating a processing procedure in the calculation of the interaction energy in the first embodiment.

As shown in FIG. 2, the control unit 12 executes the electronic state calculation processing (step S10) and the IFIE calculation processing (step S20) in this order.

Figure 3:
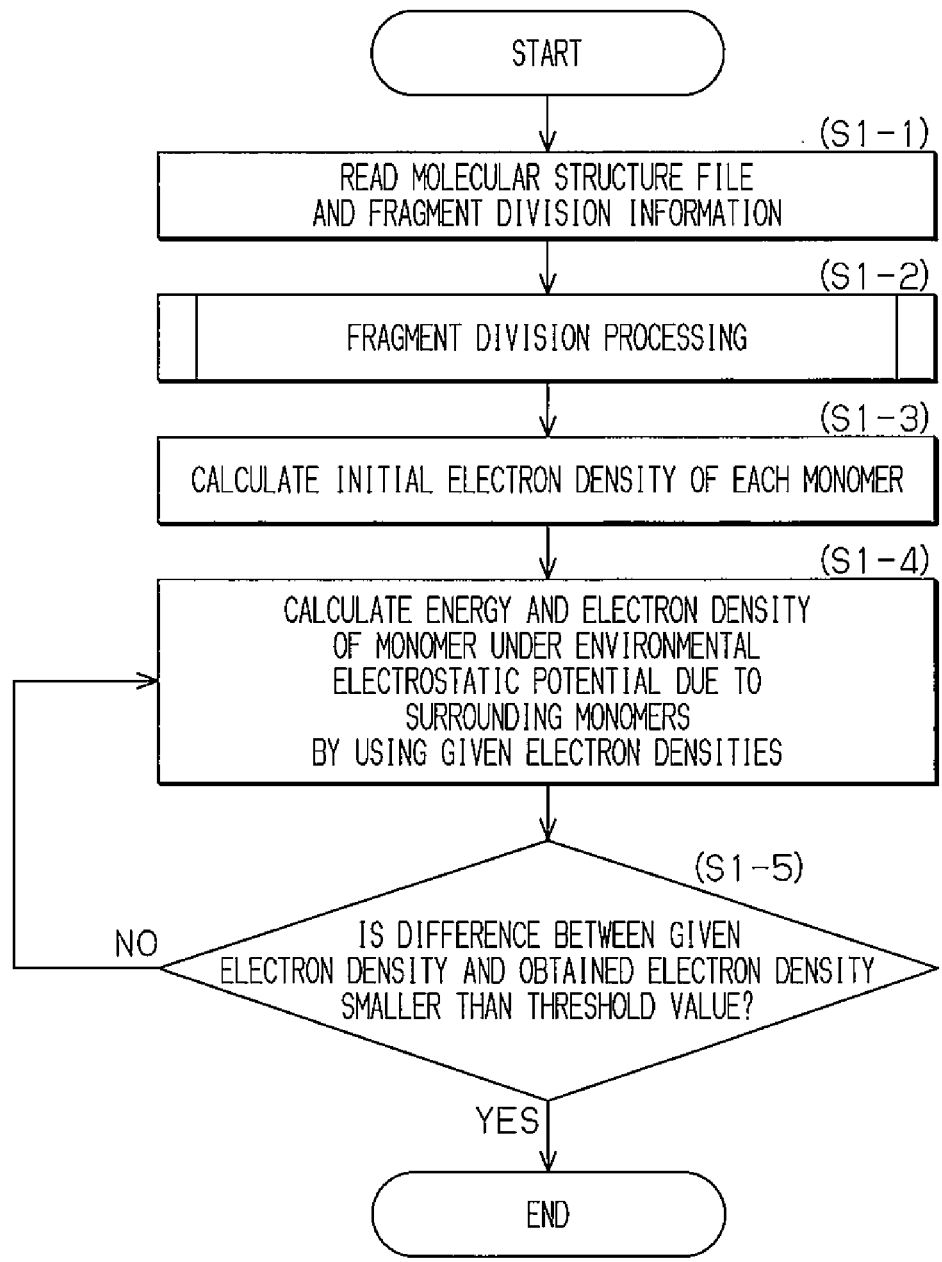
FIG. 3 is a flowchart illustrating the procedure of the electronic state calculation processing in FIG. 2.

Of these steps, in the electronic state calculation processing (step S10), as shown in FIG. 3, the control unit 12 reads the molecular structure file and the set of fragment division information (step S1-1). The monomer calculation means 12A reads the set of molecular structure data and the set of fragment division information included in the set of calculation condition data 13A.

Next, the control unit 12 performs the processing of dividing the structure of the complex into fragments (step S1-2). The monomer calculation means 12A divides each of the receptor structure and the candidate compound structure into a plurality of fragments on the basis of the set of molecular structure data and the set of fragment division information read in the preceding step S1-1. In this case, the monomer calculation means 12A allots the electrons of the covalent bonds broken in the division into fragments to the respective fragments such that each of the fragments does not become a radical. When the set of fragment division information includes a set of information indicating that the candidate compound is treated as a molecule, the candidate compound structure is not divided into fragments.

On the basis of the set of molecular structure data and the set of fragment division information, the receptor structure is divided into, for example, a plurality of fragments as shown in the following a formula a. In the formula a, a peptide composed of 11 amino acids is shown as an example of the fragment division model wherein the boundaries between the fragments are shown with dotted line segments. In this peptide, the third amino acid as counted from the N-terminal is glycine ($Gly_3$), the fourth amino acid is cysteine ($Cys_4$), and the sixth amino acid is proline ($Pro_6$), and the tenth amino acid is cysteine ($Cys_{10}$).

nuclear charges possessed by the BDA, five nuclear charges are allotted to the fragment to which the BDA belongs, and one nuclear charge is allotted to the fragment bonded to the BDA. For the receptor structure, the respective amino acid residues thus divided are each treated as one fragment. As shown in the formula a, when a disulfide bond formed between two cysteines is present in the receptor, the two cysteines are treated as one fragment.

On completion of the fragment division processing, the control unit 12 calculates the initial electron densities of the monomers belonging to each of the fragments (step S1-3). The monomer calculation means 12A reads the basis functions, the electronic state calculation method, and the set of fragment division information included in the set of calculation condition data 13A. The monomer calculation means 12A calculates the initial electron density of each of the monomers by performing the calculation on the basis of the data prepared by reading the electron density of each of the monomers wherein the monomers are each regarded as an isolated molecule. The monomer calculation means 12A causes the memory 13 to store the calculated initial electron density of each of the monomers as a part of the set of electronic state data 13B.

Next, the control unit 12 calculates the energy and the electron density of each of the monomers under the environmental electrostatic potential by using the initial electron densities, namely, the given electron densities of the respective monomers (step S1-4). The monomer calculation means 12A reads the initial electron densities of the respective monomers from the memory 13, and calculates the environmental electrostatic potential for each of the monomers from the initial electron densities of the monomers other than the monomer, present around the monomer. The monomer calculation means 12A calculates, for each of the monomers, the energy and the electron density of each of the monomers under the environmental electrostatic potential for the monomer.

Next, the control unit 12 determines whether or not the difference between the given electron density and the

[Formula 1]

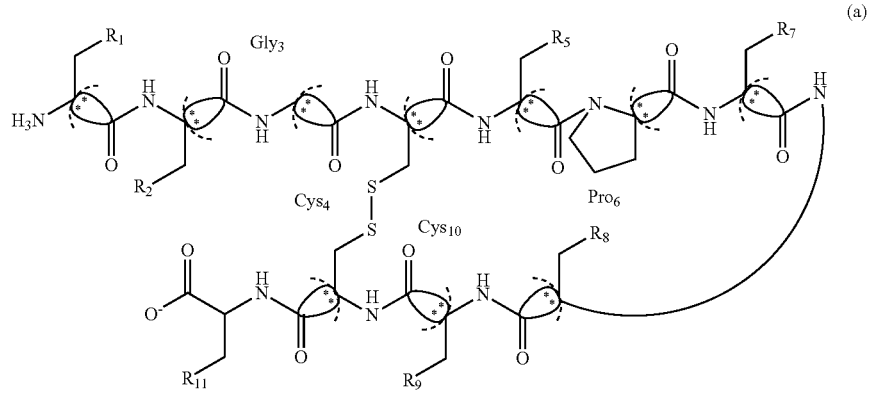

(a)

As shown in the formula a, the receptor structure is divided into, for example, a plurality of fragments, at a site between the carbon atoms in the carbonyl groups of the amino acid residues and the carbon atoms bonded to the carbon atoms, which are the α-carbons. In other words, the receptor is divided into amino acid residue units such that each of the α-carbons is a BDA (bond detached atom). Each BDA belongs to a fragment at an N-terminal side. Of the six obtained electron density is smaller than a threshold value (step S1-5). The monomer calculation means 12A acquires, for each of the monomers, the difference of the electron density in each of the monomers by comparing the initial electron density of the monomer, calculated in the step S1-3 and the electron density of the monomer under the environmental electrostatic potential of the monomer, calculated in the step S1-4. When the electron density difference in each of the monomers is smaller than the threshold value, namely, when the electron density of each of the monomers can be regarded as self-consistent (the case of "YES" in the step S1-5), the control unit 12 causes the memory 13 to store the energy and the electron density of each of the monomers, obtained in the step S1-4, and ends the electronic state calculation processing (step S10) (the first calculation stage).

On the other hand, when the electron density difference is larger than the threshold value (the case of "NO" in the step S1-5), the control unit 12 gets back to the step S1-4 and re-executes this processing. The monomer calculation means 12A uses the electron density of each of the monomers obtained in the last cycle in the step S1-4, in place of the initial electron density of the monomer, recalculates the environmental electrostatic potential of each of the monomers, due to the monomers around the monomer, and recalculates the energy and the electron density of each of the monomers under the environmental electrostatic potential of the monomer. The control unit 12 gets back to the step S1-5 and re-executes this processing. The monomer calculation means 12A compares the difference between the electron density of each of the monomers calculated in the step S1-4 in the last cycle and the electron density of each of the monomers calculated in the step S1-4 in the current cycle with the threshold value. As a result of this comparison, when the electron density differences are smaller than the threshold value (the case of "YES" in the step S1-5), the control unit 12 causes the memory 13 to store the energy and the electron density of each of the monomers, obtained in the step S1-4 in the current cycle, and ends the electronic state calculation processing. On the other hand, when the electron density differences are larger than the threshold value (the case of "NO" in the step S1-5), the control unit 12 repeats the processing of the step S1-4 and the processing of the step S1-5 until the difference between the electron density of each of the monomers calculated in the step S1-4 in the last cycle and the electron density of each of the monomers calculated in the step S1-4 in the current cycle comes to be smaller than the threshold value (the case of "YES" in the step S1-5).

Figure 4:
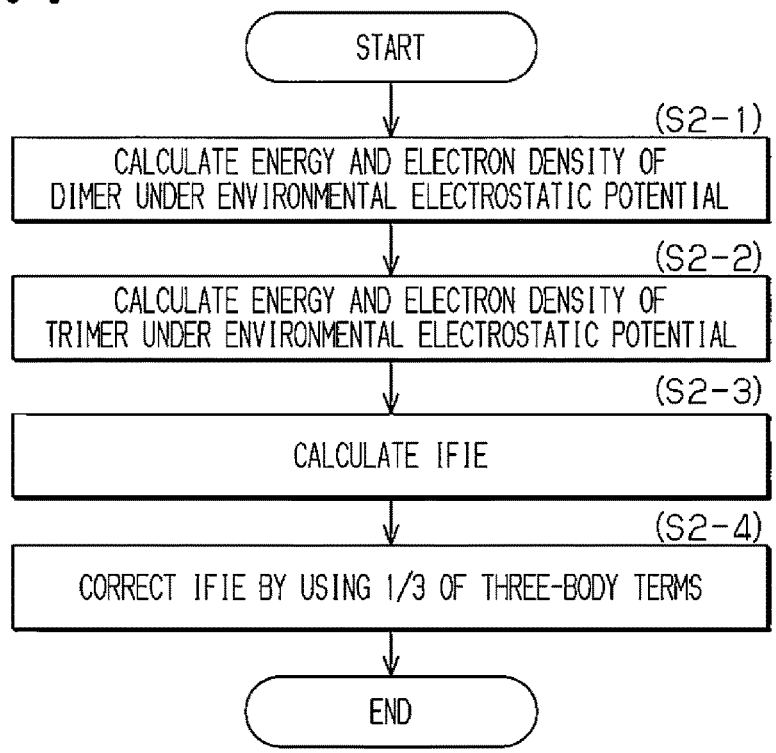
FIG. 4 is a flowchart illustrating the procedure of the IFIE calculation processing in FIG. 2.

Next, in the IFIE calculation processing (step S20), as shown in FIG. 4, for the dimer under the environmental electrostatic potential, the control unit 12 first calculates the energy and the electron density of the dimer (step S2-1). The two-body term calculation means 12B reads the energies and the electron densities of all the monomers from the set of electronic state data 13B. The two-body term calculation means 12B treats any two fragments as a dimer, and calculates the environmental electrostatic potential due to the monomers around the dimer. Successively, the two-body term calculation means 12B calculates the energy and the electron density of the dimer under the calculated environmental electrostatic potential. The two-body term calculation means 12B cause the memory 13 to store the energies and the electron densities of all the dimers different from each other as a part of the set of electronic state data 13B.

When calculating the energies of the dimers, the two-body term calculation means 12B calculates the total electronic energy $E^{FMO2}$ based on the FMO2 method by calculating each of the terms shown in the following expression 1.

[Expression 1]

$$E^{FMO2} = \sum_{I>J} \Delta E_{IJ} + \sum_{I} E_I = \sum_{I>J} \Delta \tilde{E}_{IJ} + \sum_{I} E'_I \quad (1)$$

In the equation on the left side of the expression 1, the first term of the right-hand side represents the sum of the inter-fragment interaction energies for a plurality of dimers different from each other, each under the environmental electrostatic potential. The second term of the right-hand side represents the sum of the energies of the monomers each under the environmental electrostatic potential. In the equation on the right side of the expression 1, the first term of the right-hand side represents the sum of the inter-fragment interaction energies for the dimers different from each other, each exclusive of the contribution from the environmental electrostatic potential, namely, the sum of the two-body interaction energies of the respective dimers. The second term of the right-hand side represents the sum of the energies of the respective monomers, each exclusive of the contribution from the environmental electrostatic potential.

When calculating the $E^{FMO2}$ on the basis of the expression 1, the two-body term calculation means 12B also calculates the two-body interaction energy in the foregoing specific dimer (the second calculation stage).

Next, the control unit 12 reads the energies and the electron densities of all the monomers from the set of electronic state data 13B. The three-body term calculation means 12C treats any three fragments as a trimer, and calculates the environmental electrostatic potential due to the monomers around the trimer. Next, the three-body term calculation means 12C calculates the energy and the electron density of the trimer under the calculated environmental electrostatic potential (step S2-2). The three-body term calculation means 12C causes the memory 13 to store the energies and electron densities of all the trimers different from each other as a part of the set of electronic state data 13B.

When calculating the energies of the trimers, the three-body term calculation means 12C calculates the total electronic energy $E^{FMO3}$ on the FMO3 method by calculating each of the terms shown in the following expression 2.

[Expression 2]

$$E^{FMO3} = \sum_{I>J>K} \Delta \tilde{E}_{IJK} + \sum_{I>J} \Delta \tilde{E}_{IJ} + \sum_{I} E'_I \quad (2)$$

The first term of the right-hand side in the expression 2 represents the sum of the inter-fragment interaction energies for the trimers different from each other, each exclusive of the contribution from the environmental electrostatic potential, namely, the sum of the three-body interaction energies of the respective trimers. The second term of the right-hand side is the same as the first term of the right-hand side shown in the equation on the right side in the expression 1, and the third term is the same as the second term of the right-hand side shown in the equation on the right side in the expression 1.

When calculating $E^{FMO3}$ the basis of the expression 2, the three-body term calculation means 12C also calculates the three-body interaction energies of the trimers including the foregoing specific dimer.

Next, the control unit 12 calculates the IFIE in a specific dimer (step S2-3). The IFIE calculation means 12D reads the data representing the specific dimer to be the calculation object of the interaction energy from the set of calculation condition data 13A. The IFIE calculation means 12D further reads the two-body interaction energy in the specific dimer to be the calculation object, and adopts the two-body interaction energy as the IFIE in the specific dimer. The IFIE calculation means 12D reads the three-body interaction energies of all the trimers including the specific dimer, and the sum of these three-body interaction energies are adopted as the IFIEs of the trimers including the specific dimer (the third calculation stage).

Next, the control unit 12 corrects the IFIE of the dimer by using ⅓ of the three-body terms, which are the IFIEs of the trimers (step S2-4). The IFIE calculation means 12D corrects the IFIE in the specific dimer on the basis of the following expression 3. Specifically, as shown in the following the expression 3, the IFIE calculation means 12D corrects the IFIE in the specific dimer by adding ⅓ of the IFIEs of the trimers including the specific dimer to the IFIE in the specific dimer (the correction stage). The IFIE calculation means 12D outputs the corrected IFIE in the specific dimer to the output device 14 and ends the IFIE calculation processing (step S20).

[Expression 3]

$$IFIE_{IJ}^{FMO\,3} = \Delta \tilde{E}_{IJ} + \frac{1}{3}\sum_{K} \Delta \tilde{E}_{IJK} \tag{3}$$

As described above, according to the first embodiment, the following advantages are obtained.

(1) In general, in not a few cases, the electronic state of a specific dimer is affected by the monomer(s) other than the monomers constituting the dimer. However, when the electronic state of the dimer is treated exclusively on the basis of the two monomers, the effect of the other monomer(s) is hardly reflected on the interaction energy between the two bodies. With this respect, in the first embodiment, the IFIE calculation means 12D corrects the two-body interaction energy in the specific dimer with the contribution of the specific dimer in the three-body interaction energies of the trimers including the specific dimer. The fact that the two-body interaction energy is corrected by the three-body interaction energies allows the accuracy of the interaction energy to be improved as compared to the case where no correction is applied, either in the case where the quantity of the fragments in the calculation objects such as the receptor and the candidate compound is large, or in the case where the types and the directions of the inter-fragment interactions are diversified.

(2) A trimer includes three dimers different from each other. When the three dimers equally contribute to the three-body interaction energy in one trimer, the contribution of one dimer is ⅓ of the three-body interaction energy. The IFIE calculation means 12D sets the contribution of the specific dimer at ⅓ of the three-body interaction energies, and hence further improves the accuracy of the calculation including the correction.

(3) The structure of the ligand or the candidate compound is treated as a plurality of fragments. Accordingly, the interaction energy between a part of the candidate compound structure and each of the fragments constituting the receptor structure can be calculated. Thus, for each of the partial structures in the candidate compound, a set of information indicating the degree of the interaction with the receptor can be obtained.

(4) The receptor structure is divided into fragments such that the α-carbon, which is a carbon atom bonded to a carbonyl group, will be a BDA. In other words, the receptor structure is divided at the position of an $sp^3$ carbon around which electrons are localized. Therefore, as compared to the case where the receptor structure is divided into fragment at other positions, the effect of the division into fragments on the results calculated by the FMO method can be made smaller.

Second Embodiment

An interaction energy calculation system, method and program according to a second embodiment of the present invention will be described with reference to FIGS. 5 and 6. In the present embodiment, the procedure of the IFIE calculation processing is different from that in the first embodiment. Specifically, in the present embodiment, the IFIE between two fragments is calculated from the energies of the fragments calculated by using the FMO4 method taking the four-body terms into account in addition to the energies of the fragments calculated by using the FMO2 method and the energies of the fragments calculated by using the FMO3 method. Accordingly, hereinafter, the configuration of the control unit 12 responsible for the IFIE calculation processing and the IFIE calculation processing performed by the control unit 12 will be described.

Figure 5:
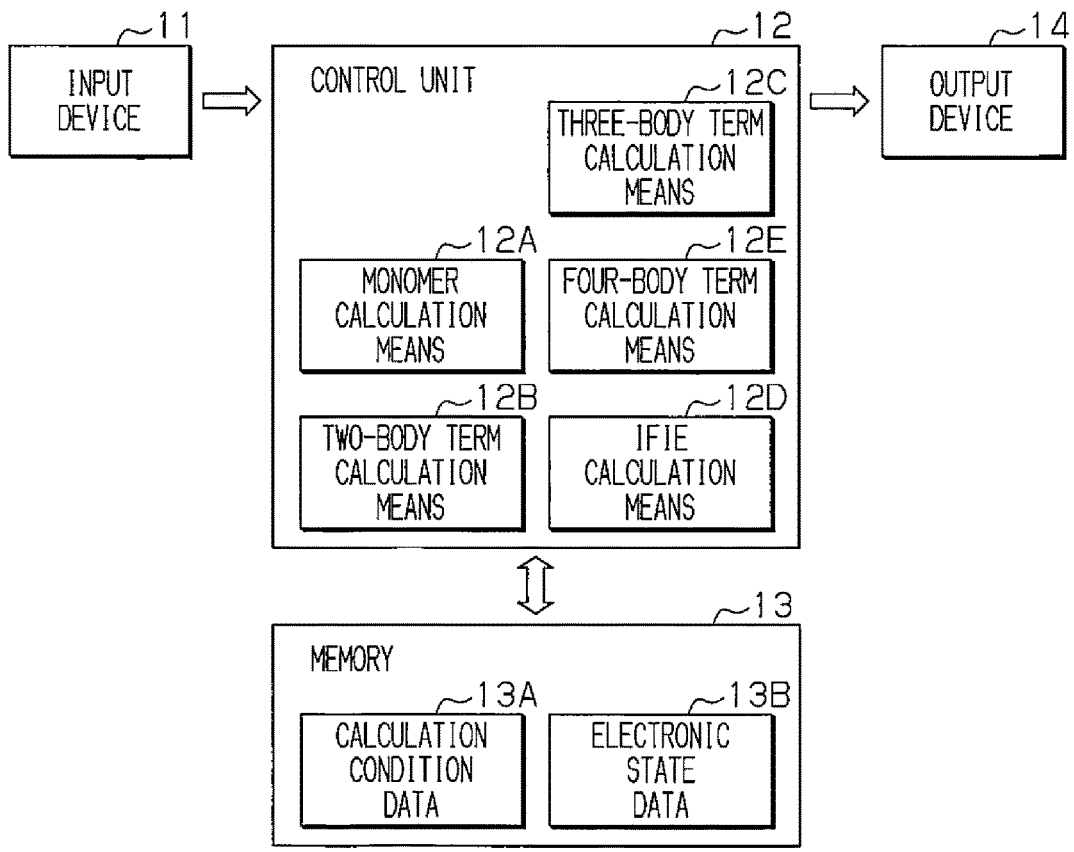
FIG. 5 is a functional block diagram illustrating the interaction energy calculation system according to a second embodiment of the present invention.

As shown in FIG. 5, the control unit 12 functions as the monomer calculation means 12A, the two-body term calculation means 12B, the three-body term calculation means 12C and the IFIE calculation means 12D, by executing the interaction energy calculation program for calculating the interaction energies. The control unit 12 further functions as a four-body term calculation means 12E serving as a fourth calculation section, by executing the interaction energy calculation program.

Among these, the monomer calculation means 12A calculates the energy and the electron density of each of the monomers each under the environmental electrostatic potential, in the same manner as in the first embodiment. The two-body term calculation means 12B also calculates the energy and the electron density of each of the dimers each under the environmental electrostatic potential, in the same manner as in the first embodiment, and the three-body term calculation means 12C also calculates the energy and the electron density of each of the trimers each under the environmental electrostatic potential, in the same manner as in the first embodiment.

The four-body term calculation means 12E treats any four fragments as a tetramer composed of the four fragments. The four-body term calculation means 12E uses the calculation results of the monomer calculation means 12A, calculates the environmental electrostatic potential of each of the tetramers, due to the monomers around the tetramer, and further calculates the energy and the electron density of each of the tetramers under the environmental electrostatic potential of the tetramer. The four-body term calculation means 12E causes the memory 13 to store the calculated energies and electron densities of the tetramers. In this case, the four-body term calculation means 12E calculates the energies and the electron density of the tetramers by using the FMO4 method. The calculation results of the four-body term calculation means 12E are stored in the memory 13.

The IFIE calculation means 12D uses the energies of the dimers calculated by the two-body term calculation means 12B, the energies of the trimers calculated by the three-body term calculation means 12C, and the energies of the tetramers calculated by the four-body term calculation means 12E, and thus calculates the IFIE in the specific dimer.

The processing procedure in the calculation of the inter-fragment interaction energies by using such an interaction energy calculation system as described above will now be described with reference to FIG. 6. The control unit 12 executes the electronic state calculation processing (step S10) and the IFIE calculation processing (step S20) in this order, in the same manner as in the first embodiment. In particular, the electronic state calculation processing is performed in the same procedure as in the first embodiment. Accordingly, hereinafter, the description of the electronic state calculation processing is omitted, and the IFIE calculation processing is exclusively described.

Figure 6:
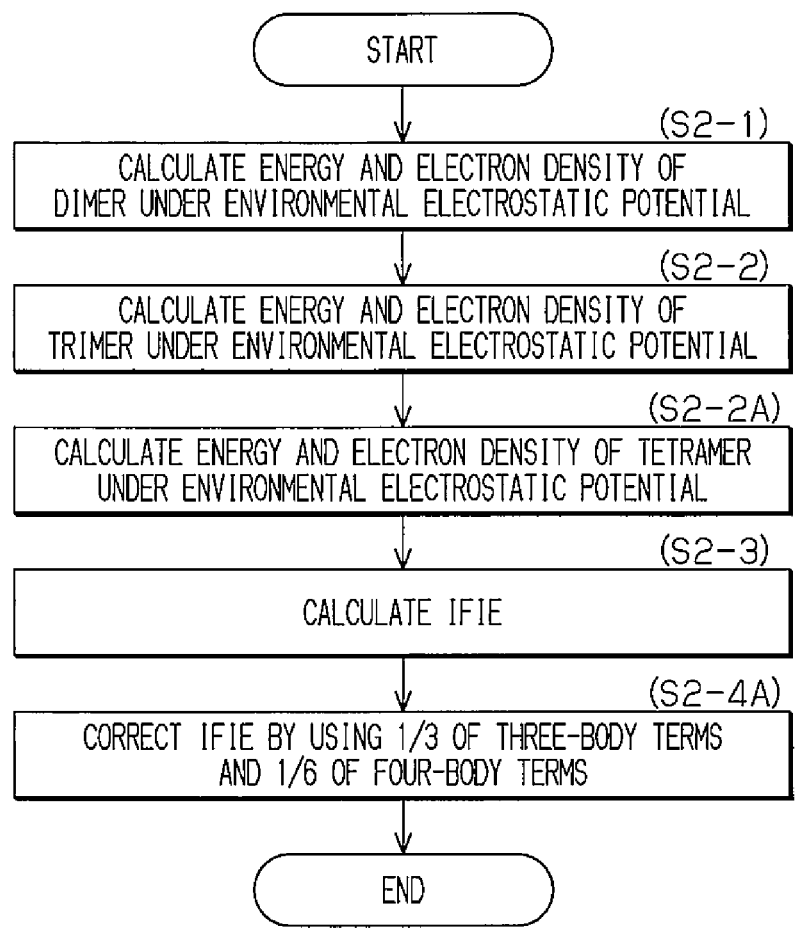
FIG. 6 is a flowchart illustrating the procedure of the IFIE calculation processing in the second embodiment.

In the IFIE calculation processing (step S20), as shown in FIG. 6, the control unit 12 first calculates the energies and the electron densities of the dimers each under the environmental electrostatic potential (step S2-1), and next calculates the energies and electron densities of the trimers each under the environmental electrostatic potential (step S2-2). In the same manner as in the first embodiment, the two-body term calculation means 12B calculates the energy and the electron density of each of the dimers each under the environmental electrostatic potential, and the three-body term calculation means 12C calculates the energy and the electron density of each of the trimers each under the environmental electrostatic potential.

Next, the control unit 12 calculates the energies and the electron densities of the tetramers each under the environmental electrostatic potential (step S2-2A). The four-body term calculation means 12E reads the energies and the electron densities of all the monomers from the set of electronic state data 13B. The four-body term calculation means 12E treats any four fragments as a tetramer, and calculates the environmental electrostatic potential due to the monomers around the tetramer. Successively, the four-body term calculation means 12E calculates the energies and the electron densities of the tetramers each under the calculated environmental electrostatic potential. The four-body term calculation means 12E causes the memory 13 to store the energies and the electron densities of all the tetramers different from each other as a part of the set of electronic state data 13B.

When calculating the energies of the tetramers, the four-body term calculation means 12E calculates the total electronic energies $E^{FMO4}$ based on the FMO4 method by calculating each of the terms shown in the following expression 4.

[Expression 4]

$$E^{FMO4} = \sum_{I>J>K>L} \Delta \tilde{E}_{IJKL} + \sum_{I>J>K} \Delta \tilde{E}_{IJK} + \sum_{I>J} \Delta \tilde{E}_{IJ} + \sum_{I} E'_I \quad (4)$$

The first term of the right-hand side in the expression 4 represents the sum of the inter-fragment interaction energies of tetramers different from each other, each exclusive of the contribution of the environmental electrostatic potential, namely, the sum of the four-body interaction energies of the respective tetramers. The second to fourth terms are the same as the first to third terms in the expression 2, respectively. When calculating $E^{FMO4}$ the basis of the expression 4, the four-body term calculation means 12E also calculates the four-body interaction energies of the tetramers including the foregoing specific dimer.

Next, the control unit 12 calculates the IFIE in a specific dimer (step S2-3). The IFIE calculation means 12D reads the data representing the specific dimer to be the calculation object of the interaction energy from the set of calculation condition data 13A, further reads the two-body interaction energy in the specific dimer to be the calculation object, and adopts the two-body interaction energy as the IFIE in the specific dimer. The IFIE calculation means 12D reads the three-body interaction energies of all the trimers including the specific dimer, and the sum of these three-body interaction energies are adopted as the IFIEs of the trimers including the specific dimer. The IFIE calculation means 12D further reads the four-body interaction energies of all the tetramers including the specific dimer, and adopts the sum of these four-body interaction energies as the IFIEs of the tetramers including the specific dimer.

Next, the control unit 12 corrects the IFIE of the dimer by using ⅓ of the three-body terms, which are the IFIEs of the trimers, and ⅙ of the four-body terms, which are the IFIEs of the tetramers (step S2-4A). The IFIE calculation means 12D corrects the IFIE in the specific dimer on the basis of the following expression 5. Specifically, as shown in the following expression 5, the IFIE calculation means 12D corrects the IFIE in the specific dimer by adding ⅓ of the IFIEs of the trimers including the specific dimer and ⅙ of the IFIEs of the tetramers including the specific dimer to the IFIE in the specific dimer. The IFIE calculation means 12D outputs the corrected IFIE in the specific dimer to the output device 14 and ends the IFIE calculation processing (step S20).

[Expression 5]

$$IFIE_{IJ}^{FMO\,4} = \Delta \tilde{E}_{IJ} + \frac{1}{3}\Delta \tilde{E}_{IJK} + \frac{1}{6}\sum_{K>L} \Delta \tilde{E}_{IJKL} \quad (5)$$

As described above, according to the second embodiment, the following advantages are obtained.

(5) The IFIE calculation means 12D corrects the two-body interaction energy in the specific dimer with the contribution of the specific dimer in the four-body interaction energies of the tetramers including the specific dimer. Accordingly, the accuracy of the interaction energy calculation is more improved as compared to the case where the correction is performed by using only the three-body interaction energy, either in the case where the quantity of the fragments in the calculation objects is large or in the case where the types and the directions of the inter-fragment interactions are diversified.

(6) A tetramer includes six dimers different from each other. When the six dimers equally contribute to the four-body interaction energy in one tetramer, the contribution of one dimer is ⅙ of the four-body interaction energy. The IFIE calculation means 12D sets the contribution of the specific dimer in the four-body interaction energy at ⅙ of the four-body interaction energies, and hence further improves the accuracy of the calculation including the correction.

Third Embodiment

An interaction energy calculation system, method and program according to a third embodiment of the present invention will be described with reference to FIGS. 7 and 8. In the present embodiment, the method for dividing the receptor structure into fragments is different from that in the first embodiment. Accordingly, hereinafter, the configuration of the control unit 12 responsible for the fragment division processing and the fragment division processing performed by the control unit 12 will be described.

Figure 7:
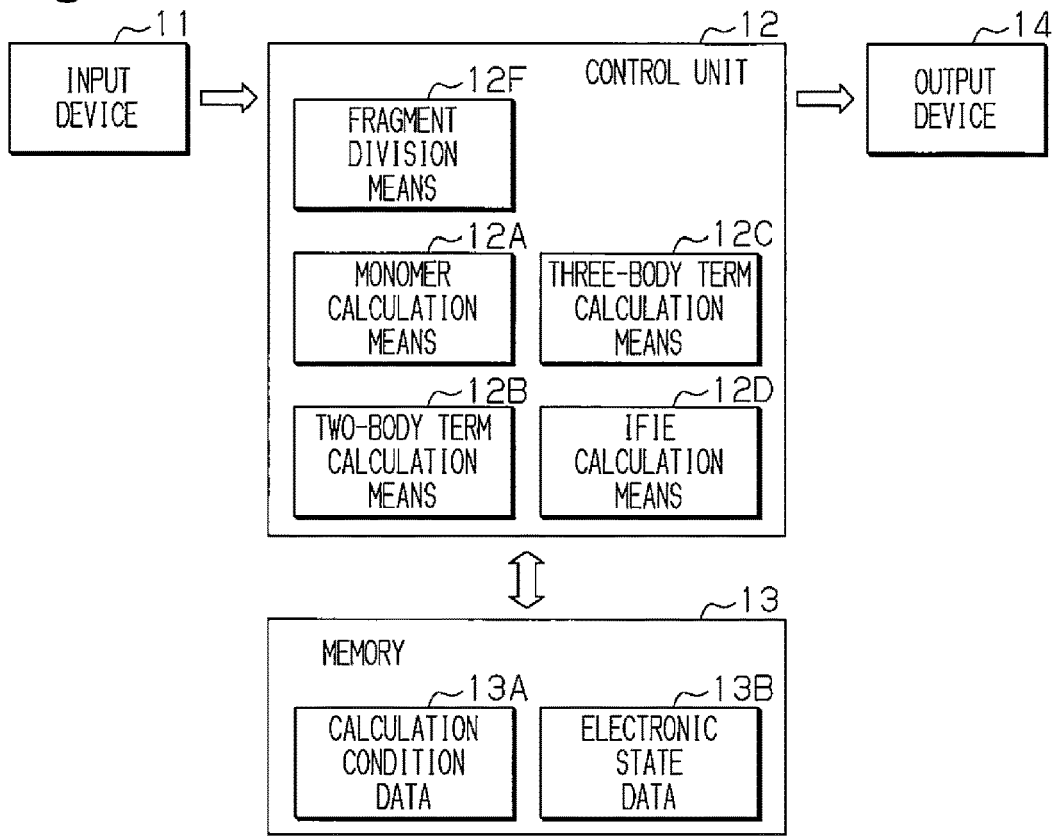
FIG. 7 is a functional block diagram illustrating the interaction energy calculation system according to a third embodiment of the present invention.

As shown in FIG. 7, the control unit 12 functions as the monomer calculation means 12A, the two-body term calculation means 12B, the three-body term calculation means 12C and the IFIE calculation means 12D, by executing the interaction energy calculation program for calculating the interaction energies. The control unit 12 further functions as a fragment division means 12F serving as a division section, by executing the interaction energy calculation program.

Among these, the fragment division means 12F divides the receptor structure into a plurality of fragments and the candidate compound structure into a plurality of fragments. In the division of the receptor into fragments, the fragment division means 12F divides the receptor structure into the fragments corresponding to the main chains of the amino acid residues and the fragments corresponding to the side chains of the amino acid residues.

For the monomers of the fragments generated by the fragment division means 12F, the monomer calculation means 12A calculates the environmental electrostatic potential of each of the monomers, due to the monomers around the monomer, and further calculates the energy and the electron density of the monomer under the environmental electrostatic potential. The monomer calculation means 12A causes the memory 13 to store the calculated energies of the monomers and the calculated electron densities of the monomers.

The two-body term calculation means 12B calculates the energy and the electron density of each of the dimers each under the environmental electrostatic potential in the same manner as in the first embodiment, and the three-body term calculation means 12C also calculates the energy and the electron density of each of the trimers each under the environmental electrostatic potential in the same manner as in the first embodiment. The IFIE calculation means 12D also calculates, in the same manner as in the first embodiment, the IFIE of a specific dimer, which is the calculation object, by using the energy of the dimer calculated by the two-body term calculation means 12B and the energies of the trimers calculated by the three-body term calculation means 12C.

The set of calculation condition data 13A stored in the memory 13 includes, in addition to the same sets of data as in the first embodiment, a main chain-side chain division command indicating the division of the amino acid residues constituting the receptor structure into the main chains and the side chains. When the set of calculation condition data 13A includes the main chain-side chain division command, the fragment division means 12F interprets the main chain-side chain division command and divides the amino acid residues into the main chains and the side chains. On the other hand, when the set of calculation condition data 13A does not include the main chain-side chain division command, the fragment division means 12F does not divide the amino acid residue into the main chains and the side chains.

Next, the processing procedure in the calculation of the inter-fragment interaction energies in the foregoing interaction energy calculation system will be described with reference to FIG. 8. The control unit 12 executes the electronic state calculation processing (step S10) and the IFIE calculation processing (step S20) in this order, in the same manner as in the first embodiment. Additionally, the electronic state calculation processing is performed in the same procedure as in the first embodiment except that the main chain-side chain division command is included in the processing procedure in the fragment division processing (step S1-2) and in the set of information read in the step S1-1. The IFIE calculation processing is also performed in the same procedure as in the first embodiment. Accordingly, hereinafter, only the fragment division processing in the electronic state calculation processing will be described, and the descriptions of the other processes are omitted.

Figure 8:
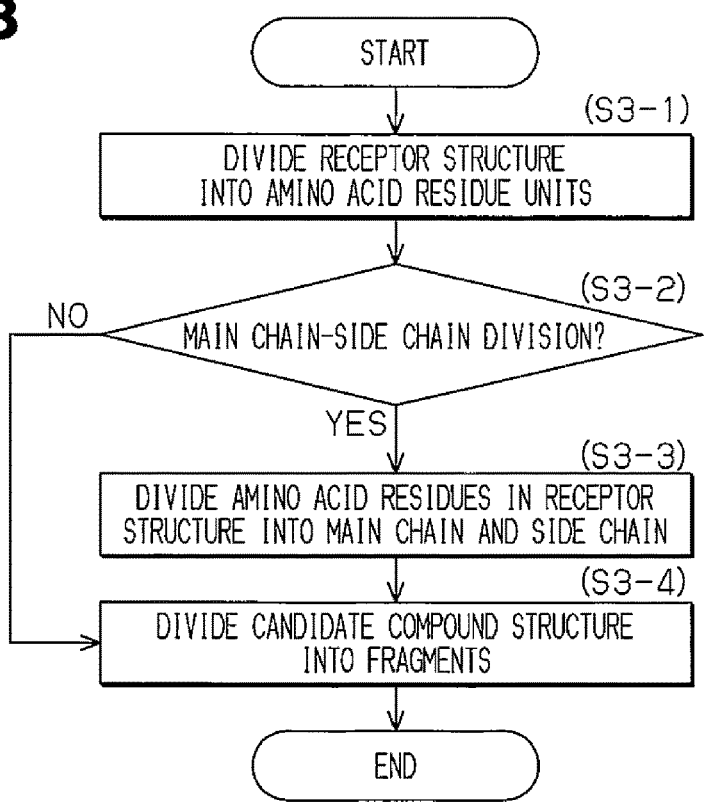
FIG. 8 is a flowchart illustrating the procedure of the fragment division processing in the third embodiment.

In the fragment division processing, as shown in FIG. 8, the control unit 12 first divides the receptor structure into amino acid residue units (step S3-1). In the same manner as in the first embodiment, the fragment division means 12F refers to the set of molecular structure data of the receptor and the set of fragment division information of the receptor, and divides the receptor structure into a plurality of fragments corresponding to the amino acid residues.

Next, the control unit 12 determines whether or not each of the amino acid residues constituting each of the fragments is divided into the fragments corresponding to the main chain of the amino acid residue and the fragments corresponding to the side chains of the amino acid residue (step S3-2). The fragment division means 12F determines whether or not the set of fragment division information includes the main chain-side chain division command. When the set of fragment division information includes the main chain-side chain division command (the case of "YES" in the step S3-2), the control unit 12 divides the amino acid residues in the receptor structure into the main chains and the side chains (step S3-3). The fragment division means 12F divides each of the amino acid residue into the fragment corresponding to the main chain of the amino acid residue and the fragments corresponding to the side chains of the amino acid residue as shown in the following formula b. In the formula b, the same peptide as in the formula a is shown as an example.

[Formula 2]

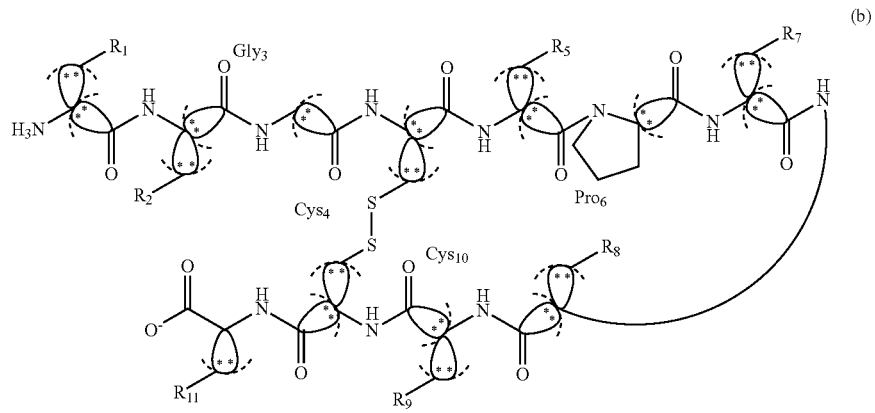

(b)

As shown in the formula b, each of the amino acid residues is divided into the main chain and the side chains such that the β-carbon bonded to the α-carbon is a BDA. Each of the BDAs belongs to the fragment composed of a side chain; of the six nuclear charges possessed by the BDA, five nuclear charges are allotted to the fragment to which the BDA belongs, and one nuclear charge is allotted to the fragment bonded to the BDA. As shown in the formula b, in glycine and proline each having no carbon bonded to α-carbon, no division of the amino acid residue is performed even when the main chain-side chain division command is executed. When a disulfide bond formed by two cysteines is present in an amino acid residue, the two cysteines are divided into two fragments each composed of a main chain and one fragment composed of both side chains such that each of the β-carbons each bonded to an α-carbon is a BDA.

Next, the control unit 12 divides the candidate compound structure into fragments (step S3-4). The fragment division means 12F refers to the molecular structure of the candidate compound and the set of fragment division information of the candidate compound, divides the candidate compound structure into a plurality of fragments, and ends the fragment division processing. When the set of fragment division information includes a set of information indicating that the candidate compound is treated as a molecule, the fragment division means 12F does not perform the division of the candidate compound.

On the other hand, when the set of calculation condition data 13A includes the main chain-side chain division command (the case of "NO" in the step S3-2), the control unit 12 does not perform the step S3-3, divides the candidate compound structure into fragments in the step S3-4, and ends the fragment division processing.

As described above, according to the third embodiment, the following advantages are obtained.

(7) The fragment division means 12F divides each of the fragments constituting the receptor into the fragments corresponding to the main chains of the amino acid residues and the fragments corresponding to the side chains of the respective amino acid residues. Accordingly, for each of the main chains and the side chains constituting the receptor structure, a set of information indicating the degree of the interaction with the candidate compound structure can be obtained.

EXAMPLES

For a molecular complex between estrogen receptor (Estrogen Receptor: ER), which was one of the nuclear receptor and 17β-estradiol (EST), which was a ligand of estrogen receptor, an energy calculation using the FMO method and the calculation of the IFIEs based on the calculated energies were performed.

Figure 9:
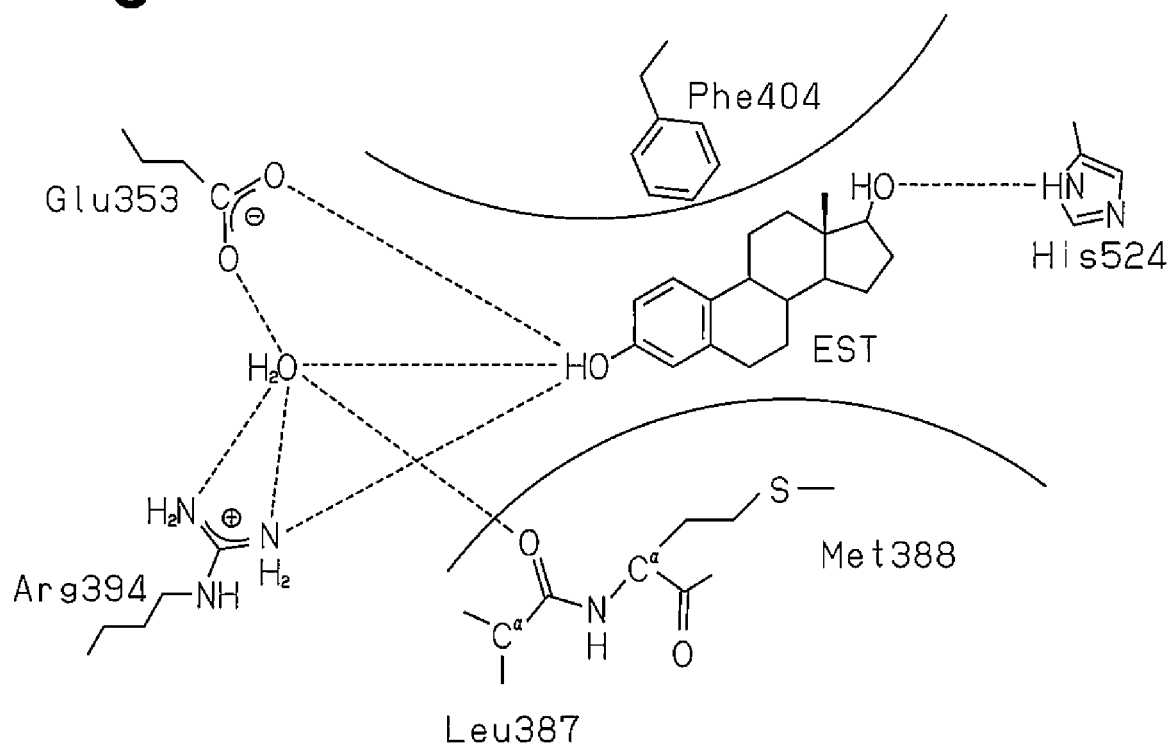
FIG. 9 is a schematic diagram illustrating the binding mode between estrogen receptor and 17β-estradiol.

The bonding between estrogen receptor and 17β-estradiol is known to be such a mode as shown in FIG. 9, from the X-ray crystal analysis of the molecular complex and various types of biochemical experiments. Specifically, as shown in FIG. 9, glutamic acid, which is the 353th amino acid in the estrogen receptor and arginine, which is the 394th amino acid in the estrogen receptor, are hydrogen-bonded to the hydroxyl group bonded to the third-position carbon in 17β-estradiol, and histidine, which is the 524th amino acid in the estrogen receptor, is hydrogen bonded to the hydroxyl group bonded to the 17th position carbon in 17β-estradiol. Leucine, which is the 387th amino acid in the estrogen receptor, is hydrogen bonded to the water molecule to which glutamine, which is 353th amino acid and arginine, which is 394th amino acid in the estrogen receptor, are hydrogen bonded. In addition, methionine, which is the 388th amino acid in the estrogen receptor, and phenylalanine, which is the 404th amino acid in the estrogen receptor interact hydrophobically with 17β-estradiol.

As the set of molecular structure data of the estrogen receptor, a peptide composed of 50 amino acid residues, included in the ligand binding domain was used. In the calculation based on the FMO method and the calculation of IFIEs, as shown in the formula b, the peptide was divided into amino acid residue units such that the α-carbons would be BDAs, and each of the amino acid residues was divided into the main chain and the side chains, and thus each of the main chain and the side chains of each of the amino acid residues was treated as one fragment.

As the set of molecular structure data of 17β-estradiol, the structure shown in the following formula c was used. The molecular complex to be the calculation object also includes one water molecule hydrogen bonded to 17β-estradiol, and in the calculation based on the FMO method and in the calculation of the IFIEs, the water molecule was treated as one fragment.

The 17β-estradiol structure was taken as one fragment, and the IFIEs between the respective amino acid residues in the receptor structure and 17β-estradiol were calculated to yield the IFIEs "without division". For the calculation of the IFIEs, the MP2 method was used as the electronic state calculation method, and the 6-31G basis functions were used as the basis functions.

[Formula 3]

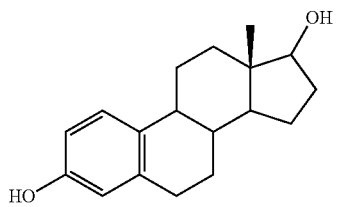

(c)

In addition, as shown in the following formula d, the covalent bond between the carbon atom at the 8th position and the carbon atom at the 14th position and the covalent bond between the carbon atom at the 9th position and the carbon atom at the 11th position were broken to divide the 17β-estradiol structure into two fragments. The IFIEs between each of the residues of the receptor and 17β-estradiol were calculated to yield the IFIEs of the "divided model 1".

[Formula 4]

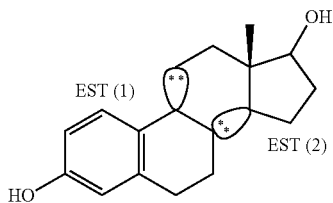

(d)

Moreover, as shown in the following formula e, the covalent bond between the 7th carbon atom and the 8th carbon atom and the covalent bond between the 9th carbon atom and the 10th carbon atom were broken to divide the 17β-estradiol structure into two fragments. The IFIEs between each of the residues of the receptor and 17β-estradiol were calculated to yield the IFIEs of the "divided model 2".

In the calculation of the IFIE of the case without division, the IFIEs of the division model 1 and the IFIEs of the division model 2, the following three types of IFIEs were calculated: the IFIE based only on the two-body terms, the IFIE to which the three-body term correction was added as in the first embodiment and the IFIE to which the three-body term correction was added and further the four-body term correction was added as in the second embodiment. The uncorrected IFIEs, the IFIEs to which the three-body term correction was added, and the IFIEs to which three-body term and four-body term corrections were added are shown in Table 1, Table 2 and Table 3, respectively.

In Table 1 to Table 3, the IFIEs between the whole receptor and each of the 17β-estradiol models represented by the formula c to the formula e, respectively, are shown as the IFIE sum. In Table 1 to Table 3, the IFIEs between several amino acid residues regarded as important in the binding with the ligand in the receptor and the 17β-estradiol models represented by the formula c to the formula e, respectively, are also shown. Moreover, in Table 1 to Table 3, the difference between each of the IFIE calculated by using the divided model 1 and the IFIE calculated by using the divided model 2 and the IFIE calculated by using the undivided 17β-estradiol structure (without division) is shown as ΔIFIE.

[Formula 5]

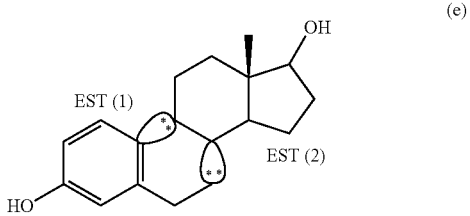

(e)

TABLE 1

Uncorrected IFIEs
FM02-MP2/6-31G

| | | | IFIE | | | ΔIFIE | |
|---|---|---|---|---|---|---|---|
| Residue No. | Residue name | Fragment | Without division | Model 1 | Model 2 | Model 1 | Model 2 |
| 353 | GLU | Main chain | 0.928 | 0.911 | 0.918 | −0.018 | −0.011 |
| 353 | GLU | Side chain | −43.035 | −42.414 | −42.444 | 0.621 | 0.591 |
| 387 | LEU | Main chain | −0.239 | −0.233 | −0.129 | 0.007 | 0.111 |
| 387 | LEU | Side chain | −2.435 | −2.447 | −2.486 | −0.012 | −0.051 |
| 388 | MET | Main chain | −0.444 | −0.255 | −0.410 | 0.189 | 0.035 |
| 388 | MET | Side chain | −1.714 | −1.636 | −0.955 | 0.079 | 0.760 |
| 394 | ARG | Main chain | −0.115 | −0.130 | −0.120 | −0.015 | −0.004 |
| 394 | ARG | Side chain | −7.448 | −7.737 | −7.627 | −0.289 | −0.179 |
| 404 | PHE | Main chain | 0.374 | 0.411 | 0.412 | 0.038 | 0.038 |
| 404 | PHE | Side chain | −4.251 | −4.323 | −3.049 | −0.072 | 1.202 |
| 524 | HIS | Main chain | −0.687 | −0.657 | −0.668 | 0.030 | 0.019 |
| 524 | HIS | Side chain | −10.354 | −10.208 | −10.396 | 0.146 | −0.042 |
| 7000 | WAT | — | −2.019 | −2.081 | −2.091 | −0.062 | −0.072 |
| | | IFIE sum | −90.165 | −87.177 | −85.634 | 2.988 | 4.531 |

TABLE 2

IFIEs corrected by using three-body terms
FM03-MP2/6-31G

| Residue No. | Residue name | Fragment | IFIE Without division | IFIE Model 1 | IFIE Model 2 | ΔIFIE Model 1 | ΔIFIE Model 2 |
|---|---|---|---|---|---|---|---|
| 353 | GLU | Main chain | 0.996 | 0.978 | 0.985 | −0.018 | −0.011 |
| 353 | GLU | Side chain | −41.517 | −40.900 | −40.934 | 0.617 | 0.583 |
| 387 | LEU | Main chain | −0.497 | −0.485 | −0.377 | 0.012 | 0.120 |
| 387 | LEU | Side chain | −2.463 | −2.469 | −2.519 | −0.006 | −0.056 |
| 388 | MET | Main chain | −0.496 | −0.301 | −0.480 | 0.195 | 0.015 |
| 388 | MET | Side chain | −1.721 | −1.723 | −1.314 | −0.002 | 0.407 |
| 394 | ARG | Main chain | −0.115 | −0.130 | −0.120 | −0.015 | −0.004 |
| 394 | ARG | Side chain | −6.674 | −6.963 | −6.855 | −0.289 | −0.180 |
| 404 | PHE | Main chain | 0.349 | 0.389 | 0.392 | 0.040 | 0.043 |
| 404 | PHE | Side chain | −4.265 | −4.378 | −3.785 | −0.113 | 0.479 |
| 524 | HIS | Main chain | −0.829 | −0.799 | −0.810 | 0.031 | 0.020 |
| 524 | HIS | Side chain | −10.337 | −10.189 | −10.376 | 0.147 | −0.040 |
| 7000 | WAT | — | −1.073 | −1.135 | −1.146 | −0.062 | −0.073 |
| | IFIE sum | | −92.479 | −90.139 | −89.481 | 2.340 | 2.998 |

TABLE 3

IFIEs corrected by using three-body and four-body terms
FM04-MP2/6-31G

| Residue No. | Residue name | Fragment | IFIE Without division | IFIE Model 1 | IFIE Model 2 | ΔIFIE Model 1 | ΔIFIE Model 2 |
|---|---|---|---|---|---|---|---|
| 353 | GLU | Main chain | 0.997 | 0.979 | 0.986 | −0.018 | −0.010 |
| 353 | GLU | Side chain | −41.736 | −41.119 | −41.151 | 0.617 | 0.585 |
| 387 | LEU | Main chain | −0.475 | −0.464 | −0.356 | 0.011 | 0.119 |
| 387 | LEU | Side chain | −2.487 | −2.497 | −2.550 | −0.010 | −0.063 |
| 388 | MET | Main chain | −0.501 | −0.305 | −0.501 | 0.195 | 0.000 |
| 388 | MET | Side chain | −1.730 | −1.737 | −1.338 | −0.006 | 0.392 |
| 394 | ARG | Main chain | −0.115 | −0.130 | −0.120 | −0.015 | −0.004 |
| 394 | ARG | Side chain | −6.786 | −7.074 | −6.965 | −0.288 | −0.179 |
| 404 | PHE | Main chain | 0.352 | 0.392 | 0.394 | 0.039 | 0.042 |
| 404 | PHE | Side chain | −4.266 | −4.376 | −3.792 | −0.111 | 0.473 |
| 524 | HIS | Main chain | −0.834 | −0.803 | −0.814 | 0.030 | 0.019 |
| 524 | HIS | Side chain | −10.354 | −10.207 | −10.394 | 0.147 | −0.040 |
| 7000 | WAT | — | −1.263 | −1.325 | −1.335 | −0.062 | −0.073 |
| | IFIE sum | | −92.889 | −90.591 | −89.994 | 2.298 | 2.894 |

Table 1 shows the uncorrected IFIEs. The ΔIFIE in the IFIE sum was 2.988 kcal/mol in the divided model 1 and 4.531 kcal/mol in the divided model 2. The difference of the ΔIFIE between the divided model 1 and the divided model 2 was 1.54 kcal/mol.

As compared with these values, in the IFIEs corrected by using the three-body terms, shown in Table 2, the ΔIFIE in the IFIE sum was 2.340 kcal/mol in the divided model 1 and 2.998 kcal/mol in the divided model 2. In this way, even when the ligand structure is divided into a plurality of fragments, the correction of the IFIEs by using the three-body terms allows the accuracy of the calculation of the IFIEs to be improved as compared to the uncorrected IFIEs. Moreover, the difference of the ΔIFIE between the divided model 1 and the divided model 2 was 0.66 kcal/mol, and thus the difference between the divided models is smaller as compared to the case where only the two-body terms are involved, namely, the case where no correction was performed. In other words, the correction by using the three-body terms yields the calculation results independent of the division method.

The ΔIFIE of the side chain of the 404th residue of phenylalanine based on the divided model 1 is −0.072 kcal/mol in terms of the uncorrected IFIE, and on the other hand, 0.113 kcal/mol in terms of the IFIE corrected by using the three-body terms. In this way, it has been found that, depending on the amino acid residue, even the IFIE corrected by using the three-body terms can be somewhat larger in the ΔIFIE as compared to the uncorrected IFIE. However, in most of the amino acid residues, the correction of the IFIEs by using the three-body terms considerably improves the ΔIFIEs. Therefore, as found in the IFIE sum, the accuracy of the IFIE calculation is improved.

In the IFIEs shown in Table 3, corrected by using the three-body terms and the four-body terms, the ΔIFIE in the IFIE sum was 2.298 kcal/mol in the divided model 1 and 2.894 kcal/mol in the divided model 2. The difference of the ΔIFIE between the divided model 1 and the divided model 2 was 0.60 kcal/mol. In this way, even when the ligand structure was divided into a plurality of fragments, the correction of the IFIEs by using the four-body terms allows the accuracy of the calculation of the IFIEs to be more improved than the uncorrected IFIEs. Moreover, the correction of the IFIEs by using the four-body terms allows the accuracy of the calculation of the IFIEs to be more improved than the IFIEs corrected by using only the three-body terms.

Fourth Embodiment

An interaction energy calculation system, method and program according to a fourth embodiment of the present invention will be described with reference to FIG. 10. In the present embodiment, the method for dividing the receptor structure into fragments is different from that in the third embodiment. Accordingly, hereinafter, the configuration of the control unit 12 responsible for the fragment division processing and the fragment division processing performed by the control unit 12 will be described.

The control unit 12 functions, in the same manner as in the third embodiment, as the monomer calculation means 12A, the two-body term calculation means 12B, the three-body term calculation means 12C, the IFIE calculation means 12D and the fragment division means 12F, by executing the interaction energy calculation program. Among these, the fragment division means 12F divides the receptor structure into fragments, at a site between the nitrogen atoms and carbon atoms in the peptide bonds between the amino acid residues in a manner different from the third embodiment.

The set of calculation condition data 13A stored in the memory 13 includes, in addition to the same sets of data as in the first embodiment, the peptide bond division command indicating the division of the receptor structure at a site between the nitrogen atoms and the carbon atoms in the peptide bonds in the receptor structure. When the set of calculation condition data 13A includes the peptide bond division is made at the peptide bonds when the structure corresponding to the receptor is divided into amino acid residue units (step S3-1A). The fragment division means 12F determines whether or not the set of calculation condition data 13A includes the peptide bond division command. When the set of calculation condition data 13A includes the peptide bond division command (the case of "YES" in the step S3-1A), the control unit 12 divides the amino acid residues in the receptor structure at the peptide bonds (step S3-1B). As shown in the following formula f, the fragment division means 12F divides the receptor structure into the amino acid residue units such that each of the carbon atoms bonded to the nitrogen atoms in the peptide bonds is a BDA. Each of the BDAs belongs to an N-terminal side fragment; of the six nuclear charges possessed by the BDA, five nuclear charges are allotted to the fragment to which the BDA belongs and one nuclear charge is allotted to the fragment bonded to the BDA. In the formula f, a peptide composed of 14 amino acids is shown as an example of the fragment division model, wherein the boundaries between the fragments are shown with dotted line segments. In this peptide, the third amino acid from the N-terminal is glycine ($Gly_3$), the fourth amino acid is cysteine ($Cys_4$), the sixth amino acid is proline ($Pro_6$), and the 12th amino acid is cysteine ($Cys_{12}$).

[Formula 6]

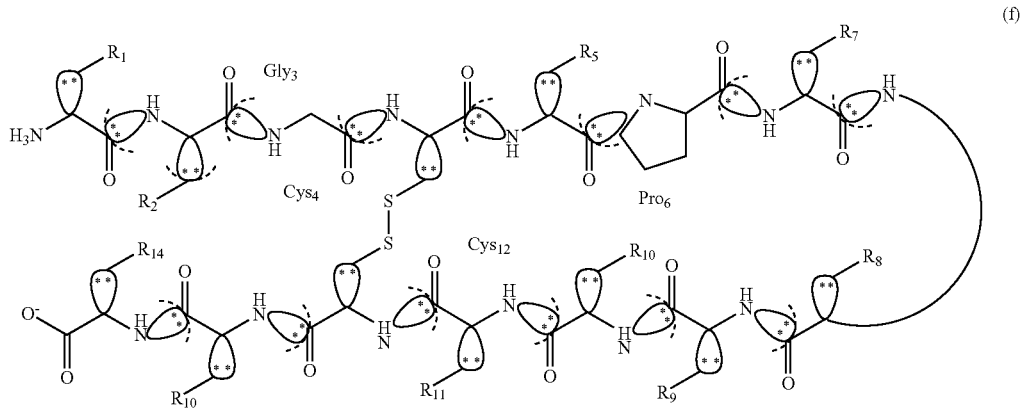

(f)

division command, the fragment division means 12F interprets the peptide bond division command and divides the amino acid residues at the peptide bonds. When the set of calculation condition data 13A does not include the peptide bond division command, the fragment division means 12F divides the receptor structure into amino acid residue units at the positions of the respective α-carbons.

Next, the processing procedure in the calculation of the inter-fragment interaction energies by using the foregoing interaction energy calculation system will be described with reference to FIG. 10. This processing procedure is the same as the processing procedure in the third embodiment except that the peptide bond division command is included in the processing procedure in the fragment division processing (step S1-2) in the electronic state calculation processing (step S10) and in the set of information read in the step S1-1. Accordingly, hereinafter, only the fragment division processing will be described, and the descriptions of the other processes are omitted.

Figure 10:
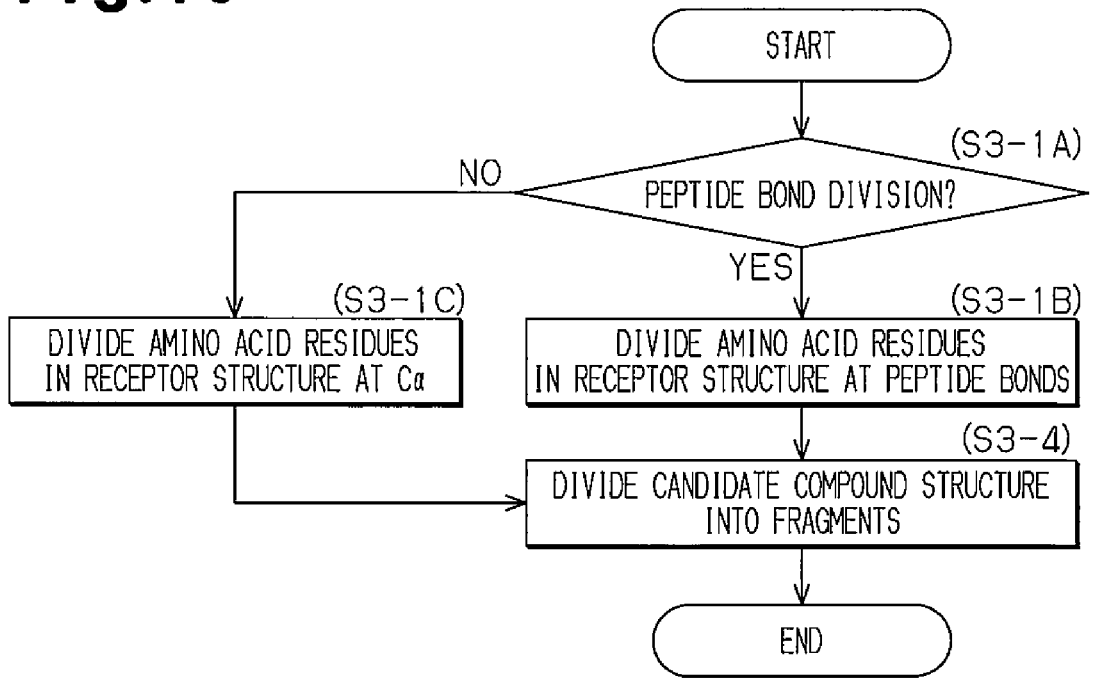
FIG. 10 is a flowchart illustrating a procedure of the fragment division processing according to a fourth embodiment.

In the fragment division processing, as shown in FIG. 10, the control unit 12 first determines whether or not the As shown in the formula f, when a disulfide bond formed between two cysteines is present in the receptor structure, the two cysteines mutually bonded by the disulfide bond are treated as one fragment in the same manner as in the first embodiment.

Next, the control unit 12 divides the candidate compound structure into a plurality of fragments (step S3-4). In the same manner as in the third embodiment, the fragment division means 12F refers to the set of molecular structure data of the candidate compound and the set of fragment division information, and thus treats the candidate compound as a plurality of fragments.

On the other hand, when the set of calculation condition data 13A does not include the peptide bond division command (the case of "NO" in the step S3-1A), the control unit 12 divides the amino acid residues in the receptor structure such that the α-carbons are the BDAs in the same manner as in the third embodiment (step S3-1C), divides the candidate compound structure into fragments, and ends the fragment division processing (step S3-4).

As described above, according to the foregoing fourth embodiment, the following advantages are obtained.

(8) The fragment division means 12F divides the receptor structure into fragments at a site between the nitrogen atoms and the carbon atoms in the peptide bonds in the receptor structure. Accordingly, the division positions of the receptor coincide with the division positions in the biochemical division of the receptor structure composed of proteins into amino acid residues. Therefore, the calculation results themselves obtained by the FMO method can be comparatively simply compared with the results obtained by biochemical experiments or the like.

Fifth Embodiment

An interaction energy calculation system, method and program according to a fifth embodiment of the present invention will be described with reference to FIG. 11. In the present embodiment, the method for dividing the receptor structure into fragments is different from that in the third embodiment. Accordingly, hereinafter, the configuration of the control unit 12 responsible for the fragment division processing and the fragment division processing performed by the control unit 12 will be described.

The control unit 12 functions, in the same manner as in the third embodiment, as the monomer calculation means 12A, the two-body term calculation means 12B, the three-body term calculation means 12C, the IFIE calculation means 12D and the fragment division means 12F, by executing the interaction energy calculation program. Among these, the fragment division means 12F divides the receptor structure into fragments, within the side chains constituting the amino acid residues in a manner different from the third embodiment.

The set of calculation condition data 13A stored in the memory 13 includes, in addition to the same sets of data as in the third embodiment, the intra-side-chain division command indicating the division of the receptor structure into fragments, within the side chains of the amino acid residues. When the set of calculation condition data 13A includes the intra-side-chain division command, the fragment division means 12F interprets the intra-side-chain division command and divides the amino acid residues into fragments, within the side chains. When the set of calculation condition data 13A does not include the intra-side-chain division command, the fragment division means 12F does not perform the division into fragments, within the side chains.

Next, the processing procedure in the calculation of the inter-fragment interaction energies by using the foregoing interaction energy calculation system will be described with reference to FIG. 11. This processing procedure is the same as the processing procedure in the third embodiment except that the intra-side-chain division command is included in the processing procedure in the fragment division processing (step S1-2) in the electronic state calculation processing (step S10) and in the set of information read in the step S1-1. Accordingly, hereinafter, only the fragment division processing will be described, and the descriptions of the other processes are omitted.

Figure 11:
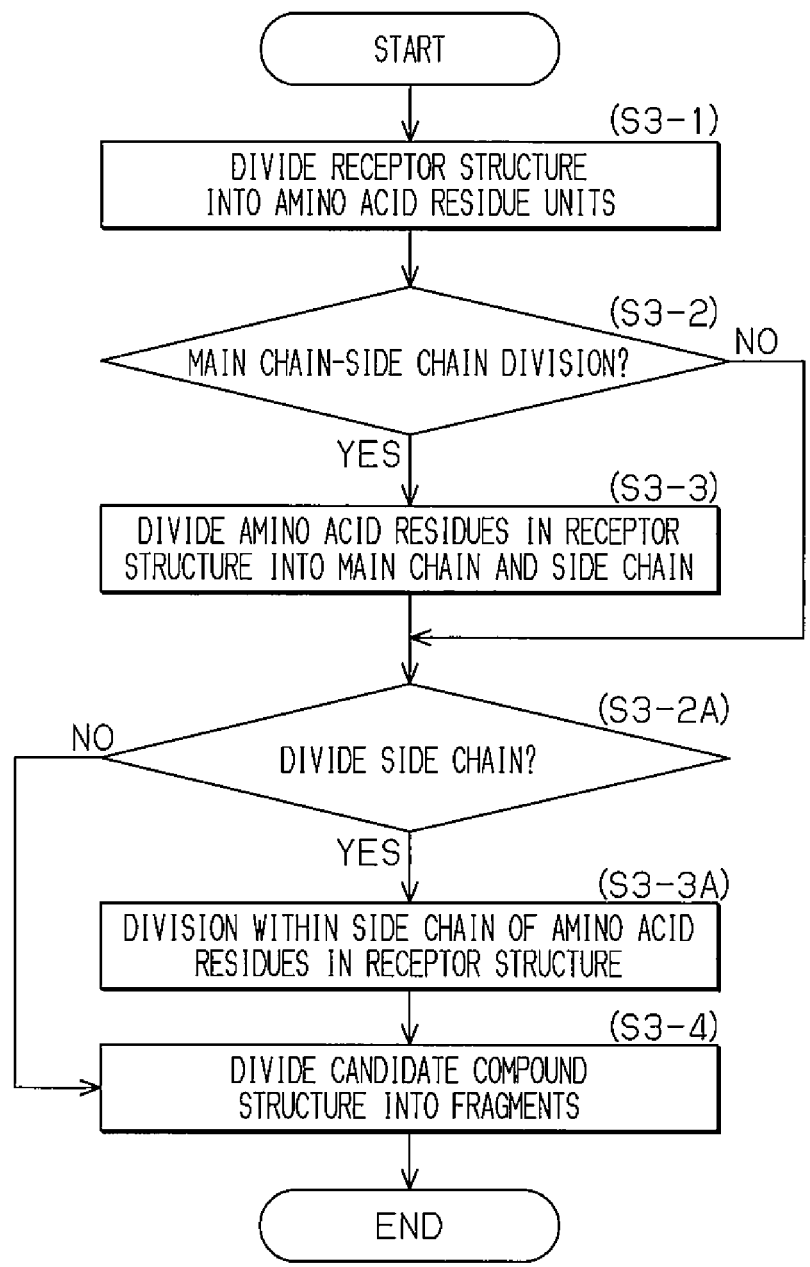
FIG. 11 is a flowchart illustrating a procedure of the fragment division processing according to a fifth embodiment.

In the fragment division processing, as shown in FIG. 11, the control unit 12 first divides the receptor structure into amino acid residue units (step S3-1). In the same manner as in the third embodiment, the fragment division means 12F refers to the set of molecular structure data of the receptor and the set of fragment division information of the receptor, and treats the receptor structure as a plurality of fragments formed by the amino acid residues.

Next, the control unit 12 determines whether or not each of the amino acid residues constituting each of the fragments is divided into the fragments composed of the main chain of the amino acid residue and the fragments composed of the side chains of the amino acid residue (step S3-2). The fragment division means 12F determines whether or not the set of calculation condition data 13A includes the main chain-side chain division command.

When the set of calculation condition data 13A includes the main chain-side chain division command (the case of "YES" in the step S3-2), the control unit 12 divides the amino acid residues in the receptor into the main chains and the side chains (step S3-3). The fragment division means 12F divides the amino acid residues into the fragments composed of the main chains and the fragments composed of the side chains. Thus, each of the fragments includes either the main chain, a partial structure of the amino acid residue or the side chain, another partial structure of the amino acid residue. On the other hand, when the set of calculation condition data 13A does not include the main chain-side chain division command (the case of "NO" in the step S3-2), the control unit 12 does not perform the step S3-3.

Next, the control unit 12 determines whether or not the division within the side chains of the amino acid residues is performed (step S3-2A). The fragment division means 12F determines whether or not the set of calculation condition data 13A includes the intra-side-chain division command.

When the set of calculation condition data 13A includes the intra-side-chain division command (the case of "YES" in the step S3-2A), the control unit 12 divides the side chains of the amino acid residues in the receptor structure (step S3-3A). As shown in the following formula g or h, the fragment division means 12F divides the receptor structure into fragments, within the side chains possessed by the amino acid residues. In the formula g and the formula h, arginine is shown as an example of the amino acid residue.

[Formula 7]

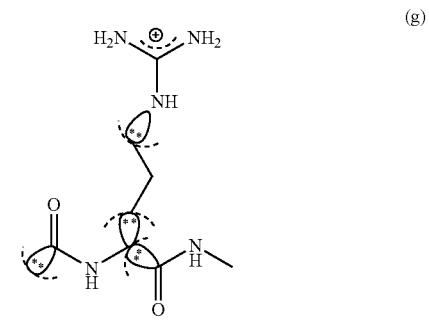

(g)

For example, when each of the amino acid residues is divided into the fragment composed of the main chain and the fragments composed of the side chains and the division within the side chains is performed, as shown in the formula g, arginine is divided such that the α-carbon, the β-carbon and the carbon atom bonded to the nitrogen atom in the side chain are BDAs. The carbon atom (BDA) bonded to the nitrogen atom in the side chain belongs to the fragment including the β-carbon. Of the six nuclear charges possessed by each of the BDAs, five nuclear charges are allotted to the fragment to which the BDA belongs and one nuclear charge is allotted to the fragment bonded to the BDA. Thus, the side chain of arginine is divided into the fragment composed of a guanidyl group having π-orbitals as a partial structure of an amino acid residue and the fragments composed of other partial structures.

[Formula 8]

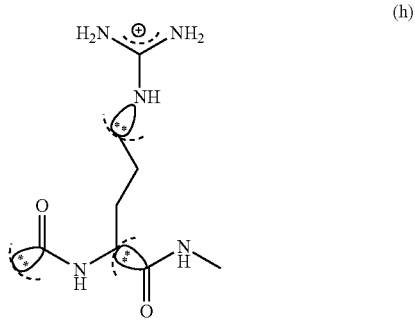

(h)

When only the division within a side-chain is performed in each of the amino acid residues, as shown in the formula h, arginine is divided such that the α-carbon and the carbon atom bonded to a nitrogen atom in the side chain are BDAs. Thus, the guanidyl group possessed by arginine is divided as a fragment.

Next, the control unit 12 divides the candidate compound structure into fragments (step S3-4). The fragment division means 12F refers to the set of molecular structure data of the candidate compound and the set of fragment division information of the candidate compound, divides the candidate compound structure into a plurality of fragments, and ends the fragment division processing. When the set of fragment division information includes a set of information for treating the candidate compound as a molecule, the fragment division means 12F does not divide the candidate compound structure.

On the other hand, when the set of calculation condition data 13A does not include the intra-side-chain division command (the case of "NO" in the step S3-2A), the control unit 12 does not perform the step S3-3A, divides the candidate compound structure into fragments in the step S3-4, and ends the fragment division processing.

As described above, according to the foregoing fifth embodiment, the following advantages are obtained.

(9) The fragment division means 12F divides each of the side chains into one or more fragments, and hence the sizes of the fragments constituting the receptor come to be equal to or smaller than the sizes of the side chains. Thus, as compared to the case where no division in the side chains is performed, the interactions between a part of the side chains and the candidate compound such as a ligand can be calculated in a state in which the effects of the other structures constituting the receptor are made smaller.

The preferred embodiments may be modified as follows.

The calculation object substance is not limited to a molecular complex composed of a receptor and a candidate compound of a ligand, but may also be a substance formed by a crystal having a periodic structure and a compound interacting with the crystal, and may also be a single crystal. In short, the calculation object substance may be a substance having a structure capable of being divided into fragments each composed of a plurality of atoms.

The contribution of a specific dimer in the three-body interaction energies may be less or larger than ⅓ of the three-body interaction energies of the trimers including the specific dimer. For example, the contribution of a specific dimer in the three-body interaction energies may be varied according to the quantity of the atoms of each of the monomers constituting the specific dimer in the quantity of atoms of each of the monomers constituting the trimer including the specific dimer.

The contribution of a specific dimer in the four-body interaction energies may be less or larger than ⅙ of the four-body interaction energies of the tetramers including the specific dimer. For example, the contribution of a specific dimer in the four-body interaction energies may be varied according to the quantity of the atoms of each of the monomers constituting the specific dimer in the quantity of atoms of each of the monomers constituting the tetramer including the specific dimer.

As shown in the following formula i, the division of the receptor structure may also be performed such that the carbon atom bonded to the nitrogen atom in a peptide bond and the β-carbon are BDAs.

[Formula 9]

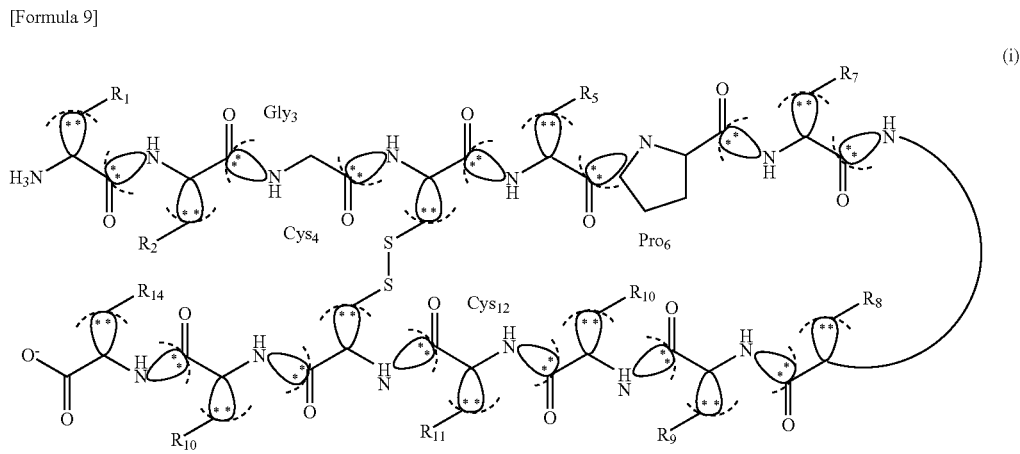

(i)

Thus, the receptor structure is divided into the fragments composed of the main chains of the respective amino acid residues and the fragments composed of the side chains of the respective amino acid residues.

In the foregoing fifth embodiment, by taking arginine as an example, the modes of the division of the receptor structure based on the division in which the α-carbon is a BDA and based on the division within a side chain are described; however, in place of the division in which the α-carbon is a BDA, a division may also be performed in which the carbon atom bonded to the nitrogen atom in a peptide bond is a BDA. When the division in which the β-carbon is a BDA is performed in addition to these divisions, as shown in a formula j, arginine is divided into the fragment composed of the main chain, the fragment composed of the guanidyl group in the side chain, and the fragment composed of the partial structure other than the guanidyl group in the side chain.

[Formula 10]

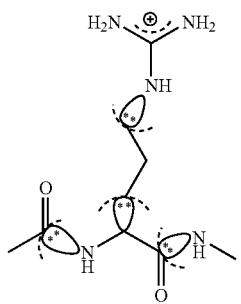

(j)

When only the division in which the carbon atom bonded to the nitrogen atom in a peptide bond is a BDA and the division in the side chain are performed, as shown in a formula k, arginine is divided into a first fragment composed of the guanidyl group in the side chain and a second fragment composed of the partial structure other than the guanidyl group in the side chain and the main chain.

[Formula 11]

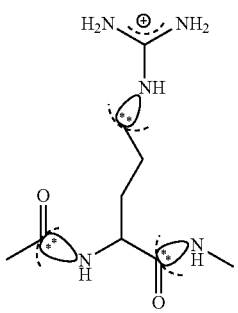

(k)

Without being limited to the case of arginine described as an example in the fifth embodiment, the division of the partial structure having π-orbitals is also possible in the amino acids such as phenylalanine, tyrosine, tryptophan and histidine. The division within the side chains of an amino acid residue is aimed at the side chains of the various amino acids, and can be performed according to the properties of the partial structure possessed by each of the side chains.

The proteins included in a calculation object substance are not limited to the nuclear receptor such as estrogen receptor, but may be a transmembrane receptor. The protein to be a calculation object substance may be an enzyme or a transporter protein. In short, the proteins included in the calculation object substance may be proteins capable of being the targets of drug discovery. The proteins included in the calculation object substance may also be proteins other than these proteins.

When the protein included in the calculation object substance is a receptor, a known ligand may also be included in the calculation object substance in place of the candidate compound of the ligand.

When the protein included in the calculation object substance is an enzyme, the calculation object substance includes a substrate subjected to an enzyme reaction or an inhibitor of an enzyme reaction, or the candidate compounds of these, in place of the ligand or the candidate compound of the ligand. In short, the calculation object substance may include a complex composed of a protein and a chemical substance to interact with the protein.

The calculation object substance may include a nucleic acid, namely, DNA or RNA and a chemical substance. The division of a nucleic acid structure is performed such that the carbon at the 5'-position of a pentose constituting each of the nucleotides is a BDA, and accordingly, the nucleic acid structure will be divided into a plurality of fragments each composed of a nucleotide.

The division of the nucleic acid structure is also performed such that the carbon at the 1'-position and the carbon at the 5'-position of a pentose are BDAs, and thus, the nucleic acid structure is divided into a first fragment composed of a pentose and phosphoric acid and a second fragment composed of a base. The fragment composed of a pentose and phosphoric acid is further divided such that the carbon at the 3'-position of the pentose is a BDA, and thus, may also be divided into a fragment composed of the pentose and a fragment composed of phosphoric acid.

As described above, in the case where the correction of IFIEs is performed by using the three-body interaction energies, or the three-body interaction energies and the four-body interaction energies, the accuracy of the IFIEs is improved even in the division into a fragment composed of a pentose and phosphoric acid and a fragment composed of a base or in the further division of the fragment composed of a pentose and phosphoric acid into the pentose and phosphoric acid. In either of the division modes, one or two or more nucleotides or nucleosides may be included in the fragment.

The IFIEs between a nucleic acid and a compound are often calculated in a state in which counter ions to neutralize the phosphoric acid of the nucleic acid, and water molecules such as the water molecules hydrogen-bonded to the nucleic acid, or the water molecules forming a hydration shell and not hydrogen-bonded to the nucleic acid are included. As described above, in the case where in the calculation of the IFIEs between a nucleic acid and a chemical substance, the correction of the IFIEs is performed by using the three-body interaction energies, or the four-body interaction energies, even when each of the counter ions and the water molecules is treated as one fragment, the IFIEs can be calculated in a state in which the accuracy is improved. With respect to the counter ions and water molecules, the whole of one or more counter ions and the whole of one or more water molecules may also each be designed to be treated as one fragment. When the calculation object substance is a protein, the calculation is also often performed in a state in which the counter ions to neutralize the charges and water molecules are included, in the same manner as for the case of a nucleic acid.

Five nuclear charges are allotted to the fragment to which the BDA belongs and one nuclear charge is allotted to the fragment bonded to the BDA. However, nuclear charges may also be allotted otherwise.

The division may also be performed in such a way that atoms other than carbon atoms become BDAs.

In each of the embodiments, the structure of the calculation object substance is divided into fragments by breaking interatomic single bonds such that the α-carbons, β-carbons or the like are be BDAs. Without being limited to this case, the structure of the calculation object substance may also be divided into fragments by breaking a double bond such that the atom double bonded to the adjacent atom is a BDA.

The total electronic energy is calculated by using the FMO2 method, the FMO3 method, and the FMO4 method. However, the energy calculation may also be performed only for the combinations of the fragments including the dimer to which attention is paid. Even in such a case, the IFIE in the dimer to which attention is paid can be calculated in the mode in which correction is performed by using the three-body interaction energy or the four-body interaction energy.

In each of the embodiments, in the calculation of the IFIEs, the two-body interaction energy is corrected by using the three-body interaction energies obtained from $E^{FMO3}$, or by using the three-body interaction energies and the four-body interaction energies obtained from $E^{FMO4}$. Without being limited to this case, a correction using the many-body terms including five or more-body terms may also be designed to be performed.

The invention claimed is:

1. An interaction energy calculation system for selecting a candidate compound based on the binding mechanism between a receptor composed of proteins and a candidate compound of a ligand to the receptor, the system comprising a control unit for calculating inter-fragment interaction energies between a plurality of monomers, which are fragments of molecules in a calculation object substance, by a fragment molecular orbital method, wherein the calculation object substance is a molecular complex including the receptor composed of proteins and the candidate compound of a ligand to the receptor,
wherein the control unit includes:
a central processing unit; and
a memory,
the control unit is configured to:
calculate the energy of each of the monomers,
calculate the total electronic energy $E^{FMO2}$ based on the FMO2 method by calculating the two-body interaction energy of each of a plurality of dimers, each of the dimers including two of the monomers, where $$E^{FMO2} = \sum_{I>J} \Delta E_{IJ} + \sum_{I} E_{I} = \sum_{I>J} \Delta \tilde{E}_{IJ} + \sum_{I} E'_{I}$$

calculate the total electronic energy $E^{FMO3}$ based on the FMO3 method by calculating the three-body interaction energy of each of a plurality of trimers, each of the trimers including three of the monomers, where $$E^{FMO3} = \sum_{I>J>K} \Delta \tilde{E}_{IJK} + \sum_{I>J} \Delta \tilde{E}_{IJ} + \sum_{I} E'_{I}$$

correct the two-body interaction energy for each dimer according to $$\Delta \tilde{E}_{IJ} + \frac{1}{3}\sum_{K} \Delta \tilde{E}_{IJK},$$

and
calculate the corrected two-body interaction energy as inter-fragment interaction energy in the dimer, wherein the control unit outputs the corrected inter-fragment interaction energy to an output device to provide the inter-fragment interaction energies between the plurality of monomers;
wherein the inter-fragment interaction energies illustrate the binding mechanism between the receptor and the candidate compound.

2. The interaction energy calculation system according to claim 1, wherein
the control unit is further configured to:
calculate the total electronic energies $E^{FMO4}$ based on the FMO4 method by calculating four-body interaction energy of each of a plurality of tetramers, each of the tetramers including four of the monomers, where $$E^{FMO4} = \sum_{I>J>K>L} \Delta \tilde{E}_{IJKL} + \sum_{I>J>K} \Delta \tilde{E}_{IJK} + \sum_{I>J} \Delta \tilde{E}_{IJ} + \sum_{I} E'_{I}$$

and
for each dimer, correct the two-body interaction energy of the dimer according to $$\Delta \tilde{E}_{IJ} + \frac{1}{3}\sum_{K} \Delta \tilde{E}_{IJK} + \frac{1}{6}\sum_{K>L} \Delta \tilde{E}_{IJKL},$$

, and
calculate the corrected two-body interaction energy as inter-fragment interaction energy in the dimer.

3. The interaction energy calculation system according to claim 1, wherein
the control unit is further configured to:
divide the structure corresponding to the calculation object substance into a plurality of monomers,
divide the receptor structure corresponding to the receptor into a plurality of monomers each including at least a partial structure of an amino acid residue, and
divide the structure corresponding to the candidate compound of the ligand into a plurality of monomers.

4. The interaction energy calculation system according to claim 3, wherein the control unit is further configured to divide the receptor structure into a monomer corresponding to a main chain of the amino acid residue and a monomer corresponding to a side chain of the amino acid residue.

5. The interaction energy calculation system according to claim 3, wherein the control unit is further configured to divide the monomer corresponding to a side chain of the amino acid residue into one or more monomers.

6. The interaction energy calculation system according to claim 3, wherein the control unit is further configured to divide the receptor structure into monomers at a site between the carbon atom in a carbonyl group of the amino acid residue and a carbon atom bonded to the carbon atom in the carbonyl group.

7. The interaction energy calculation system according to claim 3, wherein the control unit is further configured to divide the receptor structure into monomers at a site between the nitrogen atom and the carbon atom in a peptide bond between the amino acid residues.

8. A method for selecting a candidate compound based on the binding mechanism between a receptor composed of proteins and a candidate compound of a ligand to the receptor by calculating inter-fragment interaction energies between a plurality of monomers, which are fragments of molecules in a calculation object substance, wherein the calculation object substance is a molecular complex including the receptor composed of proteins and the candidate compound of a ligand to the receptor by a control unit having a central processing unit and a memory with a fragment molecular orbital method, the method comprising:

calculating, by the control unit, the energy of each of the monomers, calculating, by the control unit, the total electronic energy $E^{FMO2}$ based on the FMO2 method by calculating the two-body interaction energy of each of a plurality of dimers, each of the dimers including two of the monomers, where $$E^{FMO2} = \sum_{I>J} \Delta E_{IJ} + \sum_{I} E_I = \sum_{I>J} \Delta \tilde{E}_{IJ} + \sum_{I} E'_I$$

calculating, by the control unit, the total electronic energy $E^{FMO3}$ based on the FMO3 method by calculating the three-body interaction energy of each of a plurality of trimers, each of the trimers including three of the monomers, where $$E^{FMO3} = \sum_{I>J>K} \Delta \tilde{E}_{IJK} + \sum_{I>J} \Delta \tilde{E}_{IJ} + \sum_{I} E'_I$$

correcting, by the control unit, the two-body interaction energy for each dimer according to $$\Delta \tilde{E}_{IJ} + \frac{1}{3} \sum_{K} \Delta \tilde{E}_{IJK},$$

and calculating, by the control unit, the corrected two-body interaction energy as inter-fragment interaction energy in the dimer;

wherein the inter-fragment interaction energies illustrate the binding mechanism between the receptor and the candidate compound.

9. A non-transitory computer-readable recording medium storing a program for selecting a candidate compound based on the binding mechanism between a receptor composed of proteins and a candidate compound of a ligand to the receptor by calculating inter-fragment interaction energies between a plurality of monomers, which are fragments of molecules by using a calculating system that includes a control unit for calculating inter-fragment interaction energies between a plurality of monomers in a calculation object substance, wherein the calculation object substance is a molecular complex including the receptor composed of proteins and the candidate compound of a ligand to the receptor by a fragment molecular orbital method, the control unit including a central processing unit and a memory, wherein, when the program is executed, the computer-readable recording medium causes the control unit to:

calculate the energy of each of the monomers, calculate the total electronic energy $E^{FMO2}$ based on the FMO2 method by calculating the two-body interaction energy of each of a plurality of dimers, each of the dimers including two of the monomers, where $$E^{FMO2} = \sum_{I>J} \Delta E_{IJ} + \sum_{I} E_I = \sum_{I>J} \Delta \tilde{E}_{IJ} + \sum_{I} E'_I$$

calculate the total electronic energy $E^{FMO3}$ based on the FMO3 method by calculating the three-body interaction energy of each of a plurality of trimers, each of the trimers including three of the monomers, where $$E^{FMO3} = \sum_{I>J>K} \Delta \tilde{E}_{IJK} + \sum_{I>J} \Delta \tilde{E}_{IJ} + \sum_{I} E'_I$$

correct the two-body interaction energy for each dimer according to $$\Delta \tilde{E}_{IJ} + \frac{1}{3} \sum_{K} \Delta \tilde{E}_{IJK},$$

and calculate the corrected two-body interaction energy as inter-fragment interaction energy in the dimer;

wherein the inter-fragment interaction energies illustrate the binding mechanism between the receptor and the candidate compound.

* * * * *